United States Patent
Au et al.

(10) Patent No.: US 11,202,743 B2
(45) Date of Patent: Dec. 21, 2021

(54) PERSONAL CARE COMPOSITIONS COMPRISING FATTY ACID AMIDE DERIVATIVES

(71) Applicant: Conopco, Inc., Englewood Cliffs, NJ (US)

(72) Inventors: Van Au, Oxford, CT (US); Bijan Harichian, Irvine, CA (US); Diana Marrero, Bristol, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 122 days.

(21) Appl. No.: 16/319,580

(22) PCT Filed: Jun. 13, 2017

(86) PCT No.: PCT/EP2017/064354
§ 371 (c)(1),
(2) Date: Jan. 22, 2019

(87) PCT Pub. No.: WO2018/019463
PCT Pub. Date: Feb. 1, 2018

(65) Prior Publication Data
US 2020/0297606 A1 Sep. 24, 2020

(30) Foreign Application Priority Data
Jul. 27, 2016 (EP) .................................... 16181413

(51) Int. Cl.
| | | |
|---|---|---|
| *A61K 8/42* | (2006.01) | |
| *A61K 8/35* | (2006.01) | |
| *A61K 8/36* | (2006.01) | |
| *A61K 8/46* | (2006.01) | |
| *A61Q 5/02* | (2006.01) | |

(Continued)

(52) U.S. Cl.
CPC .................. *A61K 8/42* (2013.01); *A61K 8/35* (2013.01); *A61K 8/361* (2013.01); *A61K 8/466* (2013.01); *A61Q 5/02* (2013.01); *A61Q 5/12* (2013.01); *A61Q 17/04* (2013.01); *A61Q 19/007* (2013.01);

(Continued)

(58) Field of Classification Search
CPC .......... A61K 8/42; A61K 8/361; A61K 8/466; A61K 31/4164; A61K 8/35; A61K 31/16; A61K 2800/75; A61K 2800/782; A61K 2800/78; A61Q 19/00; A61Q 5/02; A61Q 17/04; A61Q 5/12; A61Q 19/007; A61P 43/00; A61P 17/16; A61P 25/02; A61P 29/00; A61P 17/04
See application file for complete search history.

(56) References Cited

U.S. PATENT DOCUMENTS 5,776,494 A 7/1998 Guskey et al.
6,296,859 B1 10/2001 Stoltz
(Continued)

FOREIGN PATENT DOCUMENTS

CN 1245435 2/2000
CN 1335763 2/2002
(Continued)

OTHER PUBLICATIONS

Mhaskar et al.; Synthesis of N-12-ydroxy-9-cis-octadecenoyl L-leucine and -L-leucine-L-leucine; Synthetic Communications; 1990; pp. 1305-1314; XP055396186; vol. 20, No. 9.*
Mhaskar et al. "N-Acyl-L-Leucines of biologically Active Uncommon Fatty Acids: Synthesis and Antibacterial Activity," in JAOCS, vol. 70, No. 1, 1993 (Year: 1993).*
(Continued)

*Primary Examiner* — Blessing M Fubara
(74) *Attorney, Agent, or Firm* — Edward A. Squillante, Jr.

(57) ABSTRACT

In one embodiment, the present invention provides a personal care composition, comprising:
(i) a compound of Formula (1) at a concentration from 0.0001 wt % to 20 wt % of the composition;

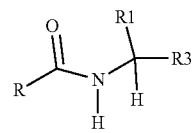

Formula (1)

wherein R is selected from the group consisting of $C_{15}$-$C_{23}$ conjugated dienes, $C_{15}$-$C_{23}$ hydroxylated mono unsaturated alkenes, and $C_{15}$-$C_{23}$ hydroxylated alkanes;
wherein R1 is selected from the group consisting of H, $C_1$-$C_4$ alkyl, —$CH_2OH$, —$CH_2(CH_3)$—OH, —$[CH_2]_4$—$NH_2$, —$CH_2$—$CO_2H$, —$[CH_2]_2$—$CO_2H$,

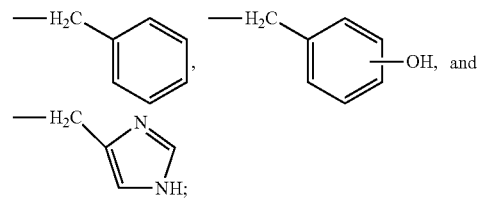

wherein R3 is —$CO_2H$; —$CH_2CO_2H$; —$CH_2CH_2CO_2H$;
and
(ii) a cosmetically acceptable carrier.

16 Claims, No Drawings

(51) Int. Cl.
*A61Q 5/12* (2006.01)
*A61Q 17/04* (2006.01)
*A61Q 19/00* (2006.01)

(52) U.S. Cl.
CPC .... *A61K 2800/75* (2013.01); *A61K 2800/782* (2013.01)

(56) References Cited

U.S. PATENT DOCUMENTS

| | | | |
|---|---|---|---|
| 6,287,553 | B1 | 11/2001 | Alaluf et al. |
| 6,440,434 | B1 | 8/2002 | Barrett et al. |
| 6,949,139 | B2 | 9/2005 | Molaire et al. |
| 8,206,691 | B2 | 6/2012 | Polonka et al. |
| 2006/0062751 | A1 | 3/2006 | Sato |
| 2011/0033404 | A1* | 2/2011 | Madison ............... A61K 8/58 424/62 |
| 2016/0136072 | A1 | 5/2016 | Klug et al. |

FOREIGN PATENT DOCUMENTS

| | | |
|---|---|---|
| CN | 1365272 | 8/2002 |
| CN | 1376051 | 10/2002 |
| CN | 1188109 | 2/2005 |
| CN | 102655845 | 9/2012 |
| CN | 103079553 | 5/2013 |
| CN | 103260594 | 8/2013 |
| CN | 105531000 | 4/2016 |
| EP | 1039902 | 3/2006 |
| EP | 2666766 | 11/2013 |
| FR | 2654107 | 5/1991 |
| FR | 2878439 | 6/2006 |
| KR | 20110088991 | 8/2011 |
| WO | WO9945899 | 9/1999 |
| WO | WO0101980 | 1/2001 |
| WO | WO0108650 | 2/2001 |
| WO | WO04061060 | 7/2004 |
| WO | WO2005115370 | 12/2005 |
| WO | WO2010060171 | 6/2010 |
| WO | WO2010136221 | 12/2010 |
| WO | WO2011054704 | 6/2011 |
| WO | WO2012061991 | 5/2012 |
| WO | WO2013014264 | 1/2013 |
| WO | WO2013149035 | 10/2013 |
| WO | WO2015040488 | 3/2015 |

OTHER PUBLICATIONS

FR2878439 A1 (using Machine translated document), Jun. 2006 (Year: 2006).*
Search Report and Written Opinion in PCTEP2017064354; dated Sep. 25, 2017.
Jurg Gertsch; Immunomodulatory Lipids in Plants: Plant Fatty Acid Amides and the Human Endocannabinoid System; Planta Med; 2008; XP007909743; pp. 638-650; vol. 74.
Da Costa Duarte et al.; New N-acylamino acids and derivatives from renewable fatty acids: gelation of hydrocarbons and thermal properties; Tetrahedron Letters; 2012; pp. 2454-2460; vol. 53; Elsevier.
Roelandt; Cannabinoid receptors 1 and 2 oppositely regulate epidermal permeability barrier status and differentiation; Experimental Dermatology; 2012; pp. 688-693; vol. 21.
Kondoh; ACyl Amino Acid Derivatives as Novel Inhibitors of Influenza Neuramindase; Bioscience Biotechnology & Biochemistry 1997 vol. 61 No. 5 pp. 870-887; 1997; pp. 870-874; vol. 61 No. 5; United States of America.
Chang; Synthesis and characterization of N-12-hydroxystearyl aminoacid-based surfactants; China Surfactant Detergent & Cosmetics Apr. 2008 vol. 38 No. 2 pp. 79-86; Apr. 2008; pp. 79-86; vol. 38 No. 2 China.
Tosum; Attenuation of serotonin-induced itch responses by inhibition of endocannabinoid degreadative enzymes fatty acid amid hydrolas; Journal of Neural Transm 2015 vol. 122 pp. 363-367; 2015; pp. 363-367.
IPRP in PCTEP2017064354; dated Jun. 5, 2018.
Cascio, et al.; A structure-activity relationship study on N-arachidonoyl-amino acids as possible endogenous inhibitors of fatty acid amide hydrolase; Biochem. and Biophyscial Research Comm.; 2004; 192-196; 314.
S.Y. Mhaskar,; N-Acyl-L-Leucines of Biologically Active Uncommon Fatty Acids: Synthesis and Antibacterial Activity; JAOCS; 1993; pp. 23-27; 70(1).
Hung The Dang, et al,; Evaluation of endogenous fatty acid amides and their synthetic analogues as potential anti-inflammatory leads; Bioorg. Med. Chem.; 2011; 1520-1527; 19.
Fatty Acid Amide Hydrolase, Inhibotor Screening Assay Kit; Cayman Chemical; unknown; pp. 1-9.

* cited by examiner

PERSONAL CARE COMPOSITIONS COMPRISING FATTY ACID AMIDE DERIVATIVES

FIELD OF THE INVENTION

The field of invention relates to personal care compositions having a variety of skin conditioning, improved exposure protection from harmful UV light and sun, and skin appearance benefits.

BACKGROUND OF THE INVENTION

Fatty acid amide hydrolase (FAAH) is an enzyme of the endocannabinoid system, and is mainly responsible for regulating the level of its main cannabinoid substrate, anandamide (AEA). Anandamide is one of the primary endogenous cannabinoids in mammals. It is formed "on demand" and mediates analgesic and anti-inflammatory effects by activation of the cannabinoid receptors CB1 and CB2. Recently, selective FAAH inhibitor URB597 was shown to attenuate serotonin-induced scratches (itch) in mice (Tosun et al., "Attenuation of serotonin-induced itch responses by inhibition of endocannabinoid degradative enzymes, fatty acid amide hydrolase and monoacylglycerol lipase", Journal of Neural Transmission (2014)). Also, CB1 and CB2 receptors themselves have recently been implicated in skin permeability barrier homeostasis and epidermal differentiation (Roelandt et al., "Cannabinoid receptors 1 and 2 oppositely regulate epidermal permeability barrier status and differentiation", Experimental Dermatology (2012), 21, 688-693.)

Surprisingly, compounds included in the inventive compositions were found to inhibit FAAH, and also to activate CB1 and/or CB2 receptors. These compounds are thus expected to provide ant-itch/anti-inflammatory benefit to skin through topical application of personal care compositions. Personal care compositions often contain surfactants, which may irritate or dry the skin of a user. Anionic surfactants especially have a tendency to irritate and to dry the skin. Yet, anionic surfactants are frequently included, particularly in the compositions which need to be lathered, e.g. shampoos. Compounds included in the present invention have an exact opposite effect (anti-itch/anti-inflammation), despite having a structure that is reminiscent of anionic surfactants, especially when present in salt form, at a higher pH—i.e. pH above 7.

Another surprising property of the compounds included in the present invention is that they boost UVA and UVB protection and boost SPF of personal compositions containing an organic sunscreen. Various cosmetic preparations have been reported for preventing and/or protecting the skin from harmful effects of ultraviolet radiation (sunburn, melanoma and formation of wrinkles and age spots and significant damage to hair). Cosmetic manufacturers aim to provide consumers with products having better and better sun protection. One of the ways of achieving this is to incorporate higher and higher levels of UVA and UVB sunscreens. One disadvantage of this approach is the high cost associated with incorporation of high levels of sunscreens which are expensive. Further, there are safety and regulatory limitations on the upper limit of incorporation of these sunscreens. Finally, sensory and physical properties are also altered on incorporation of sunscreens, particularly when the amounts of sunscreens are increased, because organic sunscreens are oily, and thus have high impact on viscosity, drying behavior, and other tactile and sensory characteristics of the formulation. Personal care compositions have a unique sensory feel that consumers come to recognize and love and associate with the particular brand or end-use. As the knowledge of the harmful effects of UV exposure developed, it became desirable to improve UVA and UVB protection substantially, without increasing levels of UVA and UVB sunscreens. This is not trivial, particularly for non-solid personal care formulations, since sunscreens tend to have high impact on viscosity, drying behavior, and other tactile and sensory characteristics of the formulation. If the feel of the formulation is altered, consumer loyalty may quickly change. It is critical to preserve the sensory profile of the composition while achieving a substantial UVA and UVB protection boost.

Surprisingly, compounds included in the personal care compositions of the invention unexpectedly deliver a significant boost in UVA/UVB protection and SPF.

SUMMARY OF THE INVENTION

In one embodiment, the present invention provides a personal care composition, comprising:
(i) a compound of Formula (1) at a concentration from 0.0001 wt % to 20 wt % of the composition;

Formula (1)

wherein R is selected from the group consisting of $C_{15}$-$C_{23}$ conjugated dienes, $C_{15}$-$C_{23}$ hydroxylated mono unsaturated alkenes, and $C_{15}$-$C_{23}$ hydroxylated alkanes;

wherein R1 is selected from the group consisting of H, $C_1$-$C_4$ alkyl, —$CH_2OH$, —$CH_2(CH_3)$—OH, —$[CH_2]_4$—$NH_2$, —$CH_2$—$CO_2H$, —$[CH_2]_2$—$CO_2H$,

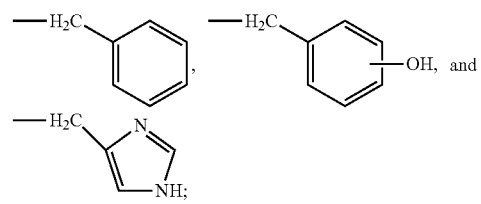

R3 is —$CO_2H$; —$CH_2CO_2H$; —$CH_2CH_2CO_2H$; and
(ii) a cosmetically acceptable carrier.

In one embodiment, the compound of Formula (1) is an anti-inflammatory agent.

In one embodiment, the compound of Formula (1) is an anti-itch agent.

In one embodiment, the compound of Formula (1) inhibits fatty acid amide hydrolase ("FAAH").

In one embodiment, the compound of Formula (1) is selected from the group consisting of a conjugated linoleic acid amide derivative, a ricinoleic acid amide derivative, a 12-hydroxystearic acid amide derivative, and mixtures thereof.

In one embodiment, the conjugated linoleic acid amide derivative is selected from the group consisting of:
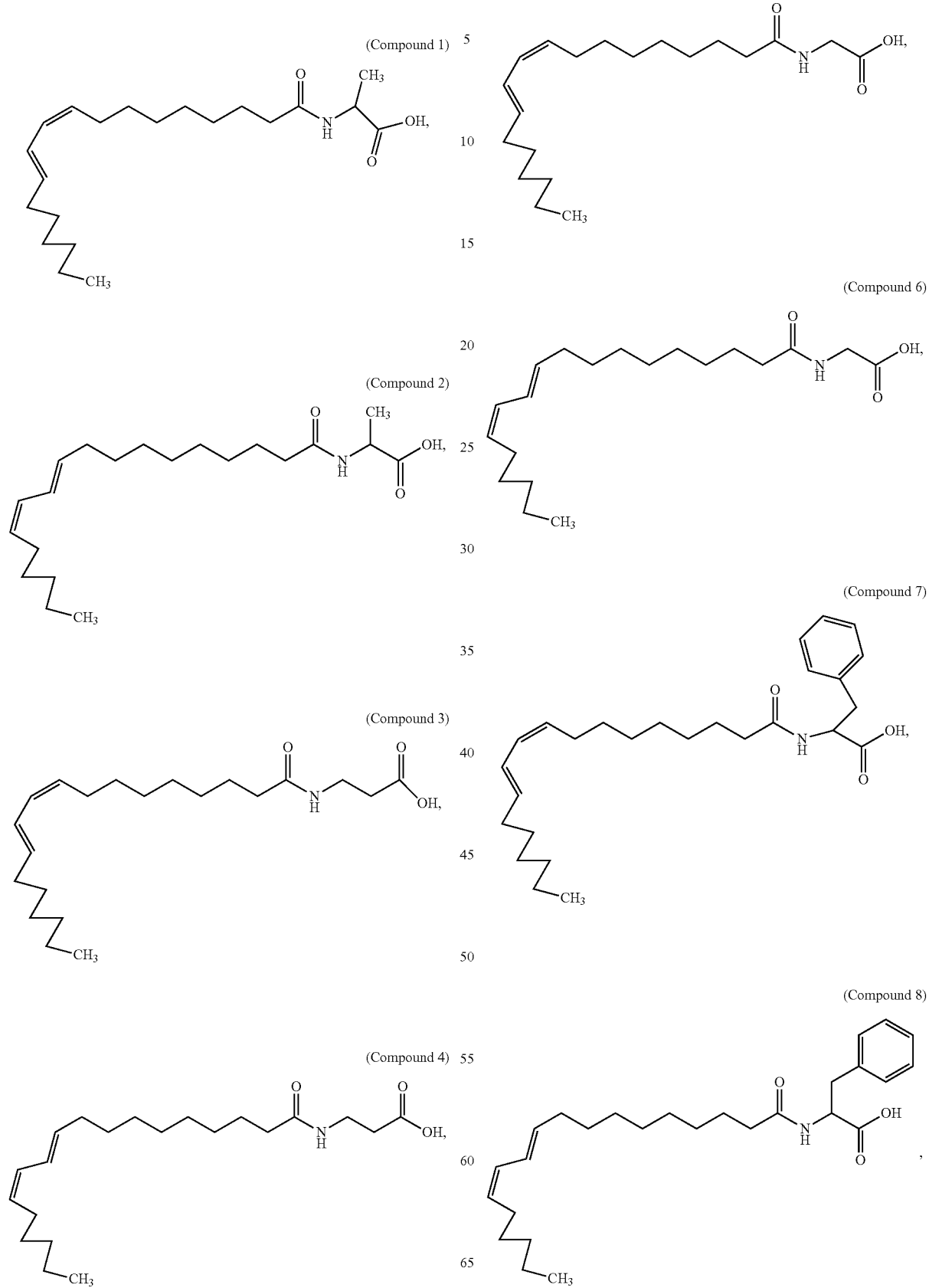

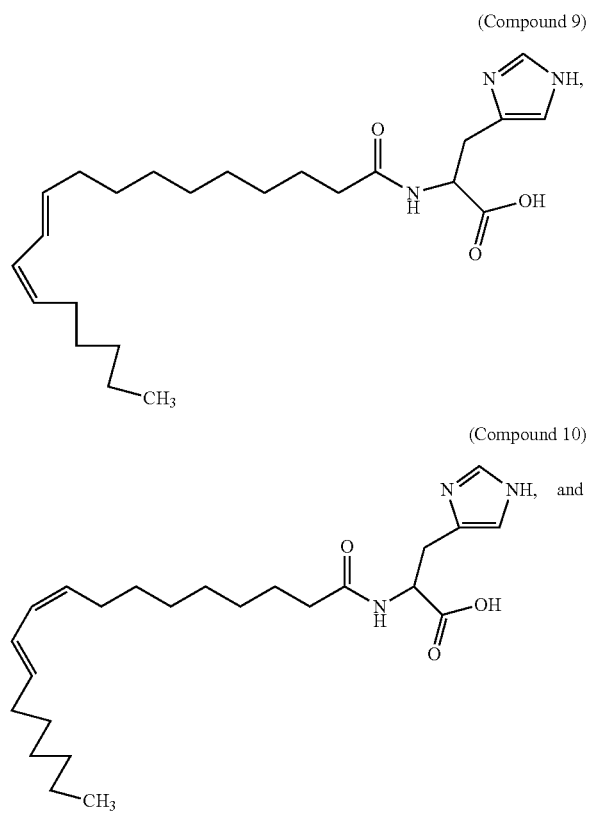
(Compound 9)
(Compound 10)
(Compound 11)
and mixtures thereof.
In one embodiment, the ricinoleic acid amide derivative is selected from the group consisting of:
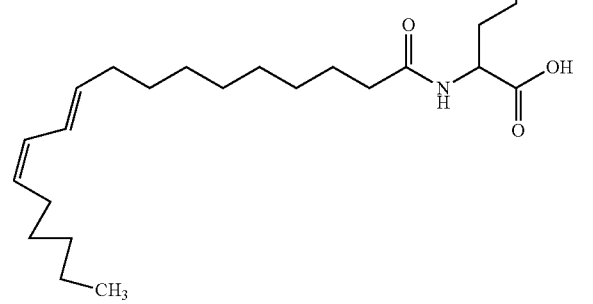
(Compound 12)
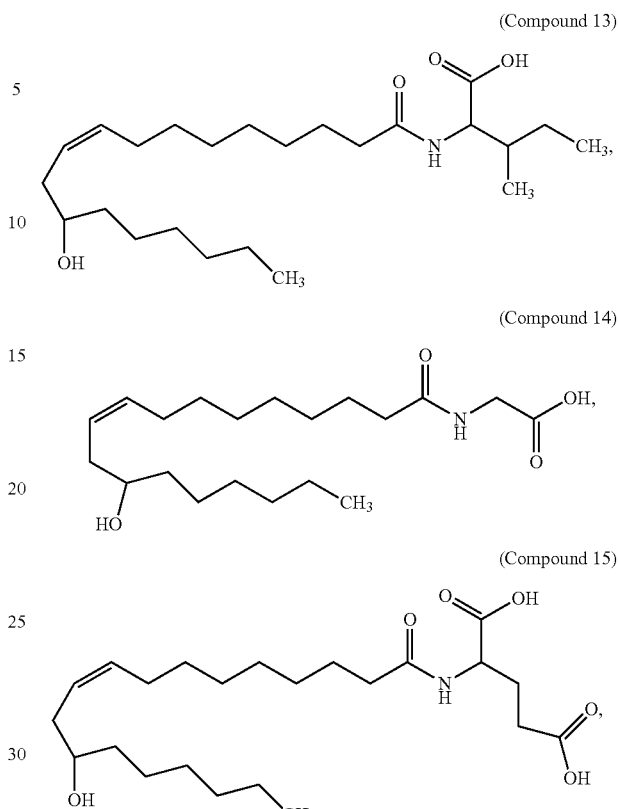
(Compound 13)
(Compound 14)
(Compound 15)
and mixtures thereof.
In one embodiment, the 12-hydroxystearic acid amide derivative is selected from the group consisting of:
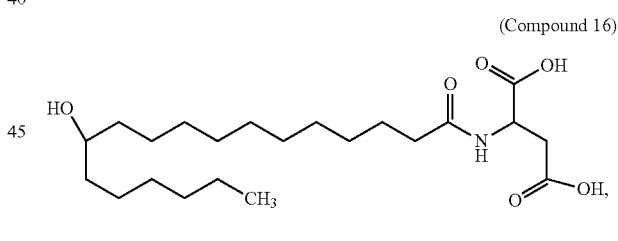
(Compound 16)
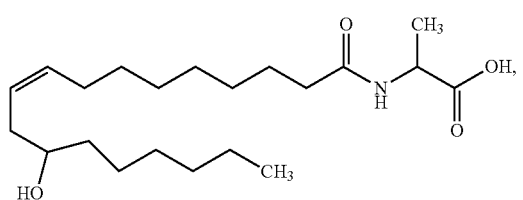
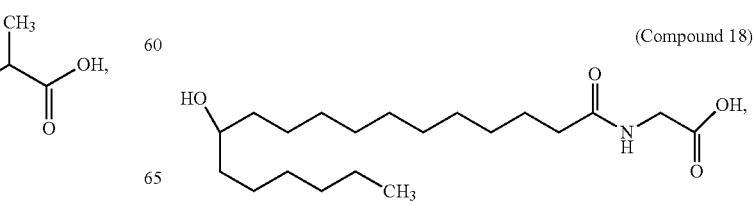
(Compound 17)
(Compound 18)

-continued

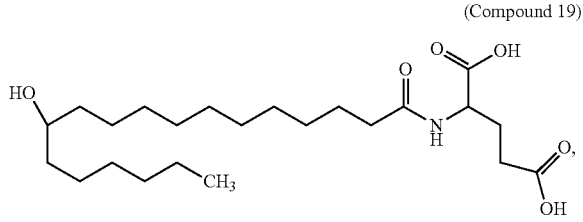

(Compound 19)

and mixtures thereof.

In one embodiment, the personal care composition is a leave-on composition, especially a non-solid composition. In one embodiment, the personal care composition is a rinse-off composition, especially a shampoo or a conditioner or scalp or hair treatment.

In one embodiment, the present invention provides a method of improving skin appearance, comprising applying the personal care composition to the skin.

In one embodiment, the present invention provides a method of boosting UVA and/or UVB protection and/or SPF of an organic sunscreen oil in the personal care composition.

In one embodiment, the present invention provides a method of reducing skin itch and/or irritation, comprising applying the personal care composition to the skin.

In one embodiment, the present invention provides a method of reducing skin dryness, comprising applying the personal care composition to the skin.

DETAILED DESCRIPTION OF THE INVENTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on." "PPAR" as used herein means peroxisome proliferator-activated receptors which are a group of nuclear receptor proteins that function as transcription factors regulating the expression of genes.

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Skin", as used herein, is meant to include skin on the face, neck, chest, back, arms (including underarms), hands, legs, buttocks and scalp.

As used herein, the term "leave-on composition" refers to a composition that is applied to the skin, hair, or body and is not intended to be washed or rinsed off for some period of time, specifically hours, as contrasted with skin or hair cleansing or wash-off or rinse-off compositions which are rinsed off or washed off immediately or minutes after the application.

As used herein, the term "personal care composition" refers to any product applied to a human body for improving appearance, sun protection, cleansing, odor control or general aesthetics and for reducing itch or irritation or inflammation. Non-limiting examples of personal care compositions include skin lotions, creams, gels, lotions, sticks, shampoos, conditioners, shower gels, toilet bars, antiperspirants, deodorants, shave creams, depilatories, lipsticks, foundations, mascara, sunless tanners and sunscreen lotions.

The personal care composition of the present technology is preferably a leave-on composition, and especially a leave-on skin care composition, because such compositions are the most challenging in terms of boosting UVA/UVB protection and/or SPF without increasing sunscreen oil amounts. Under-arm and scalp treatment compositions are also preferred, in order to deliver anti-itch, anti-dryness, anti-irritation and anti-inflammatory benefits. In an especially preferred embodiment, the cosmetic composition of this invention is a leave-on composition for topical application to skin.

In some embodiments, the present invention provides a personal care composition, comprising:
(i) a compound of Formula (1) at a concentration from 0.0001 wt % to 20 wt % of the composition;

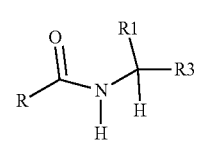

Formula (1)

wherein R is selected from the group consisting of $C_{15}$-$C_{23}$ conjugated dienes, $C_{15}$-$C_{23}$ hydroxylated mono unsaturated alkenes, and $C_{15}$-$C_{23}$ hydroxylated alkanes;

wherein R1 is selected from the group consisting of H, $C_1$-$C_4$ alkyl, —$CH_2OH$, —$CH_2(CH_3)$—OH, —$[CH_2]_4$—$NH_2$, —$CH_2$—$CO_2H$, —$[CH_2]_2$—$CO_2H$,

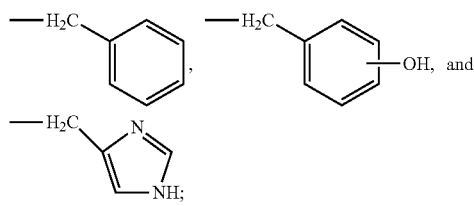

wherein R3 is —$CO_2H$; —$CH_2CO_2H$; —$CH_2CH_2CO_2H$;
and
(ii) a cosmetically acceptable carrier.

In some embodiments, the compound of Formula (1) is in the amount ranging from 0.0001 wt % to 20 wt % of the composition. Alternatively, the compound of Formula (1) is in the amount ranging from 0.01 wt % to 15 wt % of the composition. Alternatively, the compound of Formula (1) is in the amount ranging from 0.1 wt % to 12 wt % of the composition. Alternatively, the compound of Formula (1) is in the amount ranging from 0.5 wt % to 10 wt % of the composition. Alternatively, the compound of Formula (1) is in the amount ranging from 1 wt % to 5 wt % of the composition.

In some embodiments, the compound of Formula (1) is in the amount ranging from 0.0001 wt % to 5 wt % of the composition. Alternatively, the compound of Formula (1) is in the amount ranging from 0.0001 wt % to 3 wt % of the composition. Alternatively, the compound of Formula (1) is in the amount ranging from 0.0001 wt % to 2 wt % of the composition. Alternatively, the compound of Formula (1) is in the amount ranging from 0.0001 wt % to 1 wt % of the composition.

In some embodiments, the compound of Formula (1) is in the amount ranging from 1 wt % to 10 wt % of the composition. Alternatively, the compound of Formula (1) is in the amount ranging from 1 wt % to 9 wt % of the composition. Alternatively, the compound of Formula (1) is in the amount ranging from 1 wt % to 8 wt % of the composition. Alternatively, the compound of Formula (1) is in the amount ranging from 1 wt % to 4 wt % of the composition. Alternatively, the compound of Formula (1) is in the amount ranging from 1 wt % to 6 wt % of the composition. Alternatively, the compound of Formula (1) is in the amount ranging from 1 wt % to 5 wt % of the composition. Alternatively, the compound of Formula (1) is in the amount ranging from 1 wt % to 4 wt % of the composition. Alternatively, the compound of Formula (1) is in the amount ranging from 1 wt % to 3 wt % of the composition. Alternatively, the compound of Formula (1) is in the amount ranging from 1 wt % to 2 wt % of the composition.

In some embodiments, the compound of Formula (1) is in the amount ranging from 0.5 wt % to 10 wt % of the composition. Alternatively, the compound of Formula (1) is in the amount ranging from 0.5 wt % to 9 wt % of the composition. Alternatively, the compound of Formula (1) is in the amount ranging from 0.5 wt % to 8 wt % of the composition. Alternatively, the compound of Formula (1) is in the amount ranging from 0.5 wt % to 4 wt % of the composition. Alternatively, the compound of Formula (1) is in the amount ranging from 0.5 wt % to 6 wt % of the composition. Alternatively, the compound of Formula (1) is in the amount ranging from 0.5 wt % to 5 wt % of the composition. Alternatively, the compound of Formula (1) is in the amount ranging from 0.5 wt % to 4 wt % of the composition. Alternatively, the compound of Formula (1) is in the amount ranging from 0.5 wt % to 3 wt % of the composition. Alternatively, the compound of Formula (1) is in the amount ranging from 0.5 wt % to 2 wt % of the composition.

In some embodiments, the compound of Formula (1) is selected from the group consisting of a conjugated linoleic acid amide derivative, ricinoleic acid amide derivative, and a 12-hydroxystearic acid amide derivative.

In some embodiments, the compound of Formula (1) is an inhibitor of fatty acid amide hydrolase (FAAH). In some embodiments, the compound of Formula (1) that is an inhibitor of FAAH has an $IC_{50}$ between 2 μM and 50 μM. $IC_{50}$ determination assay is specifically described in the examples below. In some embodiments, the $IC_{50}$ is between 2.6 μM and 46 μM. In some embodiments, the compound of Formula (1) that is an inhibitor of FAAH has an $IC_{50}$ between 0.5 μM and 100 μM. Alternatively, the compound of Formula (1) that is an inhibitor of FAAH has an $IC_{50}$ between 0.5 μM and 90 μM. Alternatively, the compound of Formula (1) that is an inhibitor of FAAH has an $IC_{50}$ between 0.5 μM and 80 μM. Alternatively, the compound of Formula (1) that is an inhibitor of FAAH has an $IC_{50}$ between 0.5 μM and 70 μM. Alternatively, the compound of Formula (1) that is an inhibitor of FAAH has an $IC_{50}$ between 0.5 μM and 60 μM. Alternatively, the compound of Formula (1) that is an inhibitor of FAAH has an $IC_{50}$ between 0.5 μM and 50 μM. Alternatively, the compound of Formula (1) that is an inhibitor of FAAH has an $IC_{50}$ between 0.5 μM and 40 μM. Alternatively, the compound of Formula (1) that is an inhibitor of FAAH has an $IC_{50}$ between 0.5 μM and 30 μM. Alternatively, the compound of Formula (1) that is an inhibitor of FAAH has an $IC_{50}$ between 0.5 μM and 20 μM. Alternatively, the compound of Formula (1) that is an inhibitor of FAAH has an $IC_{50}$ between 0.5 μM and 10 μM. Alternatively, the compound of Formula (1) that is an inhibitor of FAAH has an $IC_{50}$ between 0.5 μM and 9 μM. Alternatively, the compound of Formula (1) that is an inhibitor of FAAH has an $IC_{50}$ between 0.5 μM and 8 μM. Alternatively, the compound of Formula (1) that is an inhibitor of FAAH has an $IC_{50}$ between 0.5 μM and 7 μM. Alternatively, the compound of Formula (1) that is an inhibitor of FAAH has an $IC_{50}$ between 0.5 μM and 6 μM. Alternatively, the compound of Formula (1) that is an inhibitor of FAAH has an $IC_{50}$ between 0.5 μM and 5 μM. Alternatively, the compound of Formula (1) that is an inhibitor of FAAH has an $IC_{50}$ between 0.5 μM and 4 μM. Alternatively, the compound of Formula (1) that is an inhibitor of FAAH has an $IC_{50}$ between 0.5 μM and 3 μM. Alternatively, the compound of Formula (1) that is an inhibitor of FAAH has an $IC_{50}$ between 0.5 μM and 2 μM. Alternatively, the compound of Formula (1) that is an inhibitor of FAAH has an $IC_{50}$ between 0.5 μM and 1 μM.

In some embodiments, the compound of Formula (1) is an inhibitor of cannabinoid receptor 1 (CB1). In some embodiments, the compound of Formula (1) that is an inhibitor of CB1 receptor binding has an $IC_{50}$ between 20 μM and 50 μM, as detected in a human receptor cell binding assay specifically described in the Examples below. In some embodiments, the $IC_{50}$ is between 22 μM and 48 μM. In some embodiments, the compound of Formula (1) that is an inhibitor of CB1 receptor binding has an $IC_{50}$ between 1 μM and 100 µM, as detected in a human receptor cell binding assay. Alternatively, the compound of Formula (1) that is an inhibitor of CB1 receptor binding has an $IC_{50}$ between 1 µM and 90 µM. Alternatively, the compound of Formula (1) that is an inhibitor of CB1 receptor binding has an $IC_{50}$ between 1 µM and 80 µM. Alternatively, the compound of Formula (1) that is an inhibitor of CB1 receptor binding has an $IC_{50}$ between 1 µM and 70 µM. Alternatively, the compound of Formula (1) that is an inhibitor of CB1 receptor binding has an $IC_{50}$ between 1 µM and 60 µM. Alternatively, the compound of Formula (1) that is an inhibitor of CB1 receptor binding has an $IC_{50}$ between 1 µM and 50 µM. Alternatively, the compound of Formula (1) that is an inhibitor of CB1 receptor binding has an $IC_{50}$ between 1 µM and 40 µM. Alternatively, the compound of Formula (1) that is an inhibitor of CB1 receptor binding has an $IC_{50}$ between 1 µM and 30 µM. Alternatively, the compound of Formula (1) that is an inhibitor of CB1 receptor binding has an $IC_{50}$ between 1 µM and 20 µM. Alternatively, the compound of Formula (1) that is an inhibitor of CB1 receptor binding has an $IC_{50}$ between 1 µM and 10 µM. Alternatively, the compound of Formula (1) that is an inhibitor of CB1 receptor binding has an $IC_{50}$ between 1 µM and 9 µM. Alternatively, the compound of Formula (1) that is an inhibitor of CB1 receptor binding has an $IC_{50}$ between 1 µM and 8 µM. Alternatively, the compound of Formula (1) that is an inhibitor of CB1 receptor binding has an $IC_{50}$ between 1 µM and 7 µM. Alternatively, the compound of Formula (1) that is an inhibitor of CB1 receptor binding has an $IC_{50}$ between 1 µM and 6 µM. Alternatively, the compound of Formula (1) that is an inhibitor of CB1 receptor binding has an $IC_{50}$ between 1 µM and 5 µM. Alternatively, the compound of Formula (1) that is an inhibitor of CB1 receptor binding has an $IC_{50}$ between 1 µM and 4 µM. Alternatively, the compound of Formula (1) that is an inhibitor of CB1 receptor binding has an $IC_{50}$ between 1 µM and 3 µM. Alternatively, the compound of Formula (1) that is an inhibitor of CB1 receptor binding has an $IC_{50}$ between 1 µM and 2 µM.

In some embodiments, the compound of Formula (1) is an inhibitor of cannabinoid receptor 2 (CB2). In some embodiments, the compound of Formula (1) that is an inhibitor of CB2 receptor binding has an $IC_{50}$ between 5 µM and 40 µM, as detected in a human receptor cell binding assay specifically described in the examples below. In some embodiments, the $IC_{50}$ is between 6 µM and 38 µM. In some embodiments, the compound of Formula (1) that is an inhibitor of CB2 receptor binding has an $IC_{50}$ between 1 µM and 100 µM. Alternatively, the compound of Formula (1) that is an inhibitor of CB2 receptor binding has an $IC_{50}$ between 1 µM and 90 µM. Alternatively, the compound of Formula (1) that is an inhibitor of CB2 receptor binding has an $IC_{50}$ between 1 µM and 80 µM. Alternatively, the compound of Formula (1) that is an inhibitor of CB2 receptor binding has an $IC_{50}$ between 1 µM and 70 µM. Alternatively, the compound of Formula (1) that is an inhibitor of CB2 receptor binding has an $IC_{50}$ between 1 µM and 60 µM. Alternatively, the compound of Formula (1) that is an inhibitor of CB2 receptor binding has an $IC_{50}$ between 1 µM and 50 µM. Alternatively, the compound of Formula (1) that is an inhibitor of CB2 receptor binding has an $IC_{50}$ between 1 µM and 40 µM. Alternatively, the compound of Formula (1) that is an inhibitor of CB2 receptor binding has an $IC_{50}$ between 1 µM and 30 µM. Alternatively, the compound of Formula (1) that is an inhibitor of CB2 receptor binding has an $IC_{50}$ between 1 µM and 20 µM. Alternatively, the compound of Formula (1) that is an inhibitor of CB2 receptor binding has an $IC_{50}$ between 1 µM and 10 µM. Alternatively, the compound of Formula (1) that is an inhibitor of CB2 receptor binding has an $IC_{50}$ between 1 µM and 9 µM. Alternatively, the compound of Formula (1) that is an inhibitor of CB2 receptor binding has an $IC_{50}$ between 1 µM and 8 µM. Alternatively, the compound of Formula (1) that is an inhibitor of CB2 receptor binding has an $IC_{50}$ between 1 µM and 7 µM. Alternatively, the compound of Formula (1) that is an inhibitor of CB2 receptor binding has an $IC_{50}$ between 1 µM and 6 µM. Alternatively, the compound of Formula (1) that is an inhibitor of CB2 receptor binding has an $IC_{50}$ between 1 µM and 5 µM. Alternatively, the compound of Formula (1) that is an inhibitor of CB2 receptor binding has an $IC_{50}$ between 1 µM and 4 µM. Alternatively, the compound of Formula (1) that is an inhibitor of CB2 receptor binding has an $IC_{50}$ between 1 µM and 3 µM. Alternatively, the compound of Formula (1) that is an inhibitor of CB2 receptor binding has an $IC_{50}$ between 1 µM and 2 µM.

In some embodiments, the irritation potential of a compound of Formula (1), as measured by the Zein solubility test method, has a Zein solubility ranging from 15% to 35%, using a 2 wt % mixture of the compound of Formula (1) in water. Zein solubility is determined as described in the Examples below. In some embodiments, a low Zein solubility results in a less irritating personal care composition according to some embodiments of the present invention.

In some embodiments, the irritation potential of a compound of Formula (1), as measured by the Zein solubility test method, has a Zein solubility ranging from 5% to 50%, using a 2 wt % mixture of the compound of Formula (1) in water. Alternatively, the irritation potential of a compound of Formula (1), as measured by the Zein solubility test method, has a Zein solubility ranging from 5% to 40%. Alternatively, the irritation potential of a compound of Formula (1), as measured by the Zein solubility test method, has a Zein solubility ranging from 5% to 30%. Alternatively, the irritation potential of a compound of Formula (1), as measured by the Zein solubility test method, has a Zein solubility ranging from 5% to 20%. Alternatively, the irritation potential of a compound of Formula (1), as measured by the Zein solubility test method, has a Zein solubility ranging from 5% to 10%. Alternatively, the irritation potential of a compound of Formula (1), as measured by the Zein solubility test method, has a Zein solubility ranging from 10% to 50%. Alternatively, the irritation potential of a compound of Formula (1), as measured by the Zein solubility test method, has a Zein solubility ranging from 10% to 40%. Alternatively, the irritation potential of a compound of Formula (1), as measured by the Zein solubility test method, has a Zein solubility ranging from 10% to 30%. Alternatively, the irritation potential of a compound of Formula (1), as measured by the Zein solubility test method, has a Zein solubility ranging from 10% to 20%. Alternatively, the irritation potential of a compound of Formula (1), as measured by the Zein solubility test method, has a Zein solubility ranging from 15% to 50%. Alternatively, the irritation potential of a compound of Formula (1), as measured by the Zein solubility test method, has a Zein solubility ranging from 15% to 40%. Alternatively, the irritation potential of a compound of Formula (1), as measured by the Zein solubility test method, has a Zein solubility ranging from 15% to 30%. Alternatively, the irritation potential of a compound of Formula (1), as measured by the Zein solubility test method, has a Zein solubility ranging from 15% to 20%.

In some embodiments, the compound of Formula (1) increases the UVA/UVB protection and sun protection factor (SPF) of the personal care composition. Without intending to be limited to any particular theory, the increase in UVA/UVB protection and SPF can result from an increase in the solubility of a sunscreen in the personal care composition of the present invention. Alternatively, the increase in sun protection factor can result from an increase in the dispersion of a sunscreen in the personal care composition of the present invention.

In some embodiments, the compound of Formula (1) increases the SPF from 20% to 125%. In some embodiments, the compound of Formula (1) increases the SPF from 20% to 120%. In some embodiments, the compound of Formula (1) increases the SPF from 20% to 115%. In some embodiments, the compound of Formula (1) increases the SPF from 20% to 110%. In some embodiments, the compound of Formula (1) increases the SPF from 20% to 105%. In some embodiments, the compound of Formula (1) increases the SPF from 20% to 100%. In some embodiments, the compound of Formula (1) increases the SPF from 20% to 95%. In some embodiments, the compound of Formula (1) increases the SPF from 20% to 90%. In some embodiments, the compound of Formula (1) increases the SPF from 20% to 85%. In some embodiments, the compound of Formula (1) increases the SPF from 20% to 80%. In some embodiments, the compound of Formula (1) increases the SPF from 20% to 75%. In some embodiments, the compound of Formula (1) increases the SPF from 20% to 70%. In some embodiments, the compound of Formula (1) increases the SPF from 20% to 65%. In some embodiments, the compound of Formula (1) increases the SPF from 20% to 60%. In some embodiments, the compound of Formula (1) increases the SPF from 20% to 55%. In some embodiments, the compound of Formula (1) increases the SPF from 20% to 50%. In some embodiments, the compound of Formula (1) increases the SPF from 20% to 45%. In some embodiments, the compound of Formula (1) increases the SPF from 20% to 40%. In some embodiments, the compound of Formula (1) increases the SPF from 20% to 35%. In some embodiments, the compound of Formula (1) increases the SPF from 20% to 30%. In some embodiments, the compound of Formula (1) increases the SPF from 20% to 25%.

In some embodiments, the compound of Formula (1) increases the solubility of a PPAR activating fatty acid in a personal care composition according to some embodiments of the present invention. In some embodiments, the PPAR activating fatty acid is selected from the group consisting of 12-hydroxystearic acid (also known as 12HSA), conjugated linoleic acid, ricinoleic acid, petroselinic acid, and mixtures thereof. In some embodiments, the PPAR activating fatty acid is selected from the group consisting of cis-9-trans-11 conjugated linoleic acid, trans-10-cis-12 conjugated linoleic acid, 7-trans octadecanoic acid, cis-parinaric acid, docosahexenoic acid, cis-4, 7, 10, 13, 16, 19 docosahexaenoic acid, ricinolaidic acid, stearidonic acid, columbinic acid, linolenelaidic acid, vaccenic acid, eicosapentanoic acid, and pinolenic acid.

In some embodiments, the conjugated linoleic acid amide derivative is selected from the group consisting of Compound 1, Compound 2, Compound 3, Compound 4, Compound 5, Compound 6, Compound 7, Compound 8, Compound 9, Compound 10, Compound 11, and mixtures thereof.

In some embodiments, the conjugated linoleic acid amide derivative is an inhibitor of fatty acid amide hydrolase (FAAH). In some embodiments, the conjugated linoleic acid amide derivative that is an inhibitor of FAAH has an $IC_{50}$ between 0.5 μM and 100 μM, as determined via the assay described in the Examples below. Alternatively, the conjugated linoleic acid amide derivative that is an inhibitor of FAAH has an $IC_{50}$ between 0.5 μM and 90 μM. Alternatively, the conjugated linoleic acid amide derivative that is an inhibitor of FAAH has an $IC_{50}$ between 0.5 μM and 80 μM. Alternatively, the conjugated linoleic acid amide derivative that is an inhibitor of FAAH has an $IC_{50}$ between 0.5 μM and 70 μM. Alternatively, the conjugated linoleic acid amide derivative that is an inhibitor of FAAH has an $IC_{50}$ between 0.5 μM and 60 μM. Alternatively, the conjugated linoleic acid amide derivative that is an inhibitor of FAAH has an $IC_{50}$ between 0.5 μM and 50 μM. Alternatively, the conjugated linoleic acid amide derivative that is an inhibitor of FAAH has an $IC_{50}$ between 0.5 μM and 40 μM. Alternatively, the conjugated linoleic acid amide derivative that is an inhibitor of FAAH has an $IC_{50}$ between 0.5 μM and 30 μM. Alternatively, the conjugated linoleic acid amide derivative that is an inhibitor of FAAH has an $IC_{50}$ between 0.5 μM and 20 μM. Alternatively, the conjugated linoleic acid amide derivative that is an inhibitor of FAAH has an $IC_{50}$ between 0.5 μM and 10 μM. Alternatively, the conjugated linoleic acid amide derivative that is an inhibitor of FAAH has an $IC_{50}$ between 0.5 μM and 9 μM. Alternatively, the conjugated linoleic acid amide derivative that is an inhibitor of FAAH has an $IC_{50}$ between 0.5 μM and 8 μM. Alternatively, the conjugated linoleic acid amide derivative that is an inhibitor of FAAH has an $IC_{50}$ between 0.5 μM and 7 μM. Alternatively, the conjugated linoleic acid amide derivative that is an inhibitor of FAAH has an $IC_{50}$ between 0.5 μM and 6 μM. Alternatively, the conjugated linoleic acid amide derivative that is an inhibitor of FAAH has an $IC_{50}$ between 0.5 μM and 5 μM. Alternatively, the conjugated linoleic acid amide derivative that is an inhibitor of FAAH has an $IC_{50}$ between 0.5 μM and 4 μM. Alternatively, the conjugated linoleic acid amide derivative that is an inhibitor of FAAH has an $IC_{50}$ between 0.5 μM and 3 μM. Alternatively, the conjugated linoleic acid amide derivative that is an inhibitor of FAAH has an $IC_{50}$ between 0.5 μM and 2 μM. Alternatively, the conjugated linoleic acid amide derivative that is an inhibitor of FAAH has an $IC_{50}$ between 0.5 μM and 1 μM. In some embodiments, the conjugated linoleic acid amide derivative that is an inhibitor of FAAH has an $IC_{50}$ between 2 μM and 50 μM. In some embodiments, the $IC_{50}$ is between 2.6 μM and 46 μM.

In some embodiments, the conjugated linoleic acid amide derivative is an inhibitor of cannabinoid receptor 1 (CB1). In some embodiments, the conjugated linoleic acid amide derivative that is an inhibitor of CB1 receptor binding has an $IC_{50}$ between 1 μM and 100 μM, as detected in a human receptor cell binding assay described in the Examples below. Alternatively, the conjugated linoleic acid amide derivative that is an inhibitor of CB1 receptor binding has an $IC_{50}$ between 1 μM and 90 μM. Alternatively, the conjugated linoleic acid amide derivative that is an inhibitor of CB1 receptor binding has an $IC_{50}$ between 1 μM and 80 μM. Alternatively, the conjugated linoleic acid amide derivative that is an inhibitor of CB1 receptor binding has an $IC_{50}$ between 1 μM and 70 μM. Alternatively, the conjugated linoleic acid amide derivative that is an inhibitor of CB1 receptor binding has an $IC_{50}$ between 1 μM and 60 μM. Alternatively, the conjugated linoleic acid amide derivative that is an inhibitor of CB1 receptor binding has an $IC_{50}$ between 1 μM and 50 μM. Alternatively, the conjugated linoleic acid amide derivative that is an inhibitor of CB1 receptor binding has an $IC_{50}$ between 1 μM and 40 μM. Alternatively, the conjugated linoleic acid amide derivative that is an inhibitor of CB1 receptor binding has an $IC_{50}$ between 1 µM and 30 µM. Alternatively, the conjugated linoleic acid amide derivative that is an inhibitor of CB1 receptor binding has an $IC_{50}$ between 1 µM and 20 µM. Alternatively, the conjugated linoleic acid amide derivative that is an inhibitor of CB1 receptor binding has an $IC_{50}$ between 1 µM and 10 µM. Alternatively, the conjugated linoleic acid amide derivative that is an inhibitor of CB1 receptor binding has an $IC_{50}$ between 1 µM and 9 µM. Alternatively, the conjugated linoleic acid amide derivative that is an inhibitor of CB1 receptor binding has an $IC_{50}$ between 1 µM and 8 µM. Alternatively, the conjugated linoleic acid amide derivative that is an inhibitor of CB1 receptor binding has an $IC_{50}$ between 1 µM and 7 µM. Alternatively, the conjugated linoleic acid amide derivative that is an inhibitor of CB1 receptor binding has an $IC_{50}$ between 1 µM and 6 µM. Alternatively, the conjugated linoleic acid amide derivative that is an inhibitor of CB1 receptor binding has an $IC_{50}$ between 1 µM and 5 µM. Alternatively, the conjugated linoleic acid amide derivative that is an inhibitor of CB1 receptor binding has an $IC_{50}$ between 1 µM and 4 µM. Alternatively, the conjugated linoleic acid amide derivative that is an inhibitor of CB1 receptor binding has an $IC_{50}$ between 1 µM and 3 µM. Alternatively, the conjugated linoleic acid amide derivative that is an inhibitor of CB1 receptor binding has an $IC_{50}$ between 1 µM and 2 µM. In some embodiments, the conjugated linoleic acid amide derivative is an inhibitor of cannabinoid receptor 1 (CB1). In some embodiments, the conjugated linoleic acid amide derivative that is an inhibitor of CB1 receptor binding has an $IC_{50}$ between 20 µM and 50 µM, as detected in a human receptor cell binding assay. In some embodiments, the $IC_{50}$ is between 22 µM and 48 µM.

In some embodiments, the conjugated linoleic acid amide derivative is an inhibitor of cannabinoid receptor 2 (CB2). In some embodiments, the conjugated linoleic acid amide derivative that is an inhibitor of CB2 receptor binding has an $IC_{50}$ between 1 µM and 100 µM, as detected in a human receptor cell binding assay. Alternatively, the conjugated linoleic acid amide derivative that is an inhibitor of CB2 receptor binding has an $IC_{50}$ between 1 µM and 90 µM. Alternatively, the conjugated linoleic acid amide derivative that is an inhibitor of CB2 receptor binding has an $IC_{50}$ between 1 µM and 80 µM. Alternatively, the conjugated linoleic acid amide derivative that is an inhibitor of CB2 receptor binding has an $IC_{50}$ between 1 µM and 70 µM. Alternatively, the conjugated linoleic acid amide derivative that is an inhibitor of CB2 receptor binding has an $IC_{50}$ between 1 µM and 60 µM. Alternatively, the conjugated linoleic acid amide derivative that is an inhibitor of CB2 receptor binding has an $IC_{50}$ between 1 µM and 50 µM. Alternatively, the conjugated linoleic acid amide derivative that is an inhibitor of CB2 receptor binding has an $IC_{50}$ between 1 µM and 40 µM. Alternatively, the conjugated linoleic acid amide derivative that is an inhibitor of CB2 receptor binding has an $IC_{50}$ between 1 µM and 30 µM. Alternatively, the conjugated linoleic acid amide derivative that is an inhibitor of CB2 receptor binding has an $IC_{50}$ between 1 µM and 20 µM. Alternatively, the conjugated linoleic acid amide derivative that is an inhibitor of CB2 receptor binding has an $IC_{50}$ between 1 µM and 10 µM. Alternatively, the conjugated linoleic acid amide derivative that is an inhibitor of CB2 receptor binding has an $IC_{50}$ between 1 µM and 9 µM. Alternatively, the conjugated linoleic acid amide derivative that is an inhibitor of CB2 receptor binding has an $IC_{50}$ between 1 µM and 8 µM. Alternatively, the conjugated linoleic acid amide derivative that is an inhibitor of CB2 receptor binding has an $IC_{50}$ between 1 µM and 7 µM. Alternatively, the conjugated linoleic acid amide derivative that is an inhibitor of CB2 receptor binding has an $IC_{50}$ between 1 µM and 6 µM. Alternatively, the conjugated linoleic acid amide derivative that is an inhibitor of CB2 receptor binding has an $IC_{50}$ between 1 µM and 5 µM. Alternatively, the conjugated linoleic acid amide derivative that is an inhibitor of CB2 receptor binding has an $IC_{50}$ between 1 µM and 4 µM. Alternatively, the conjugated linoleic acid amide derivative that is an inhibitor of CB2 receptor binding has an $IC_{50}$ between 1 µM and 3 µM. Alternatively, the conjugated linoleic acid amide derivative that is an inhibitor of CB2 receptor binding has an $IC_{50}$ between 1 µM and 2 µM. In some embodiments, the conjugated linoleic acid amide derivative is an inhibitor of cannabinoid receptor 2 (CB2). In some embodiments, the conjugated linoleic acid amide derivative that is an inhibitor of CB2 receptor binding has an $IC_{50}$ between 5 µM and 40 µM, as detected in a human receptor cell binding assay. In some embodiments, the $IC_{50}$ is between 6 µM and 38 µM.

In some embodiments, the ricinoleic acid amide derivative is selected from the group consisting of Compound 12, Compound 13, Compound 14, Compound 15, and mixtures thereof.

In some embodiments, the ricinoleic acid amide derivative that is an inhibitor of FAAH has an $IC_{50}$ between 0.5 µM and 100 µM, as determined via the assay described in the Examples below. Alternatively, the ricinoleic acid amide derivative that is an inhibitor of FAAH has an $IC_{50}$ between 0.5 µM and 90 µM. Alternatively, the ricinoleic acid amide derivative that is an inhibitor of FAAH has an $IC_{50}$ between 0.5 µM and 80 µM. Alternatively, the ricinoleic acid amide derivative that is an inhibitor of FAAH has an $IC_{50}$ between 0.5 µM and 70 µM. Alternatively, the ricinoleic acid amide derivative that is an inhibitor of FAAH has an $IC_{50}$ between 0.5 µM and 60 µM. Alternatively, the ricinoleic acid amide derivative that is an inhibitor of FAAH has an $IC_{50}$ between 0.5 µM and 50 µM. Alternatively, the ricinoleic acid amide derivative that is an inhibitor of FAAH has an $IC_{50}$ between 0.5 µM and 40 µM. Alternatively, the ricinoleic acid amide derivative that is an inhibitor of FAAH has an $IC_{50}$ between 0.5 µM and 30 µM. Alternatively, the ricinoleic acid amide derivative that is an inhibitor of FAAH has an $IC_{50}$ between 0.5 µM and 20 µM. Alternatively, the ricinoleic acid amide derivative that is an inhibitor of FAAH has an $IC_{50}$ between 0.5 µM and 10 µM. Alternatively, the ricinoleic acid amide derivative that is an inhibitor of FAAH has an $IC_{50}$ between 0.5 µM and 9 µM. Alternatively, the ricinoleic acid amide derivative that is an inhibitor of FAAH has an $IC_{50}$ between 0.5 µM and 8 µM. Alternatively, the ricinoleic acid amide derivative that is an inhibitor of FAAH has an $IC_{50}$ between 0.5 µM and 7 µM. Alternatively, the ricinoleic acid amide derivative that is an inhibitor of FAAH has an $IC_{50}$ between 0.5 µM and 6 µM. Alternatively, the ricinoleic acid amide derivative that is an inhibitor of FAAH has an $IC_{50}$ between 0.5 µM and 5 µM. Alternatively, the ricinoleic acid amide derivative that is an inhibitor of FAAH has an $IC_{50}$ between 0.5 µM and 4 µM. Alternatively, the ricinoleic acid amide derivative that is an inhibitor of FAAH has an $IC_{50}$ between 0.5 µM and 3 µM. Alternatively, the ricinoleic acid amide derivative that is an inhibitor of FAAH has an $IC_{50}$ between 0.5 µM and 2 µM. Alternatively, the ricinoleic acid amide derivative that is an inhibitor of FAAH has an $IC_{50}$ between 0.5 µM and 1 µM. In some embodiments, the ricinoleic acid amide derivative is an inhibitor of fatty acid amide hydrolase (FAAH). In some embodiments, the ricinoleic acid amide derivative that is an inhibitor of FAAH has an $IC_{50}$ between 20 μM and 50 μM. In some embodiments, the $IC_{50}$ is between 26 μM and 42 μM.

In some embodiments, the 12-hydroxystearic acid amide derivative is selected from the group consisting of Compound 16, Compound 17, Compound 18, Compound 19, and mixtures thereof.

In some embodiments, the 12-hydroxystearic acid amide derivative that is an inhibitor of FAAH has an $IC_{50}$ between 0.5 μM and 100 μM, as determined via the assay described in the Examples below. Alternatively, the 12-hydroxystearic acid amide derivative that is an inhibitor of FAAH has an $IC_{50}$ between 0.5 μM and 90 μM. Alternatively, the 12-hydroxystearic acid amide derivative that is an inhibitor of FAAH has an $IC_{50}$ between 0.5 μM and 80 μM. Alternatively, the 12-hydroxystearic acid amide derivative that is an inhibitor of FAAH has an $IC_{50}$ between 0.5 μM and 70 μM. Alternatively, the 12-hydroxystearic acid amide derivative that is an inhibitor of FAAH has an $IC_{50}$ between 0.5 μM and 60 μM. Alternatively, the 12-hydroxystearic acid amide derivative that is an inhibitor of FAAH has an $IC_{50}$ between 0.5 μM and 50 μM. Alternatively, the 12-hydroxystearic acid amide derivative that is an inhibitor of FAAH has an $IC_{50}$ between 0.5 μM and 40 μM. Alternatively, the 12-hydroxystearic acid amide derivative that is an inhibitor of FAAH has an $IC_{50}$ between 0.5 μM and 30 μM. Alternatively, the 12-hydroxystearic acid amide derivative that is an inhibitor of FAAH has an $IC_{50}$ between 0.5 μM and 20 μM. Alternatively, the 12-hydroxystearic acid amide derivative that is an inhibitor of FAAH has an $IC_{50}$ between 0.5 μM and 10 μM. Alternatively, the 12-hydroxystearic acid amide derivative that is an inhibitor of FAAH has an $IC_{50}$ between 0.5 μM and 9 μM. Alternatively, the 12-hydroxystearic acid amide derivative that is an inhibitor of FAAH has an $IC_{50}$ between 0.5 μM and 8 μM. Alternatively, the 12-hydroxystearic acid amide derivative that is an inhibitor of FAAH has an $IC_{50}$ between 0.5 μM and 7 μM. Alternatively, the 12-hydroxystearic acid amide derivative that is an inhibitor of FAAH has an $IC_{50}$ between 0.5 μM and 6 μM. Alternatively, the 12-hydroxystearic acid amide derivative that is an inhibitor of FAAH has an $IC_{50}$ between 0.5 μM and 5 μM. Alternatively, the 12-hydroxystearic acid amide derivative that is an inhibitor of FAAH has an $IC_{50}$ between 0.5 μM and 4 μM. Alternatively, the 12-hydroxystearic acid amide derivative that is an inhibitor of FAAH has an $IC_{50}$ between 0.5 μM and 3 μM. Alternatively, the 12-hydroxystearic acid amide derivative that is an inhibitor of FAAH has an $IC_{50}$ between 0.5 μM and 2 μM. Alternatively, the 12-hydroxystearic acid amide derivative that is an inhibitor of FAAH has an $IC_{50}$ between 0.5 μM and 1 μM.

In some embodiments, the 12-hydroxystearic acid amide derivative is an inhibitor of fatty acid amide hydrolase (FAAH). In some embodiments, the 12-hydroxystearic acid amide derivative that is an inhibitor of FAAH has an $IC_{50}$ between 40 μM and 50 μM. In some embodiments, the $IC_{50}$ is between 40 μM and 46 μM.

In some embodiments, the pH of the personal care composition is less than pH 8. In some embodiments, the pH of the personal care composition is between pH 3.5 and pH 8. In some embodiments, the pH of the personal care composition is between pH 5 to pH 7.8. In some embodiments, the pH of the personal care composition is less than pH 7.5. In some embodiments, the pH of the personal care composition is between 5 and 7.5, or 5.5 and 7.5. At lower pH values, the compounds included in the present invention are present predominantly in an acidic (rather than salt) form which is believed to be active form for FAAH inhibition.

Cosmetically Acceptable Carriers

Skin Care Compositions: In some embodiments, the skin care compositions of the present invention also include a cosmetically acceptable carrier. In some embodiments, where the personal care composition is a skin care composition, the cosmetically acceptable carrier is a carrier in which the compound of Formula (1) is soluble. In some embodiments, the cosmetically acceptable carrier is a lipophilic carrier that is liquid at temperatures up to 40° C.

The amount of the cosmetically acceptable carrier may vary in the skin care compositions according to some embodiments of the present invention. In some embodiments, the amount of the cosmetically acceptable carrier in a skin care composition may range from 1 to 99.9% by weight of the composition. Alternatively, the amount of the cosmetically acceptable carrier in a skin care composition may range from 70% to 95% by weight of the composition. Alternatively, the amount of the cosmetically acceptable carrier may range from 80% to 90% by weight of the composition. Alternatively, the amount of the cosmetically acceptable carrier may range from 5 to 99.9% by weight of the composition. Alternatively, the amount of the cosmetically acceptable carrier may range from 10 to 99.9% by weight of the composition. Alternatively, the amount of the cosmetically acceptable carrier may range from 15 to 99.9% by weight of the composition. Alternatively, the amount of the cosmetically acceptable carrier may range from 20 to 99.9% by weight of the composition. Alternatively, the amount of the cosmetically acceptable carrier may range from 25 to 99.9% by weight of the composition. Alternatively, the amount of the cosmetically acceptable carrier may range from 30 to 99.9% by weight of the composition. Alternatively, the amount of the cosmetically acceptable carrier may range from 35 to 99.9% by weight of the composition. Alternatively, the amount of the cosmetically acceptable carrier may range from 40 to 99.9% by weight of the composition. Alternatively, the amount of the cosmetically acceptable carrier may range from 45 to 99.9% by weight of the composition. Alternatively, the amount of the cosmetically acceptable carrier may range from 50 to 99.9% by weight of the composition. Alternatively, the amount of the cosmetically acceptable carrier may range from 55 to 99.9% by weight of the composition. Alternatively, the amount of the cosmetically acceptable carrier may range from 60 to 99.9% by weight of the composition. Alternatively, the amount of the cosmetically acceptable carrier may range from 65 to 99.9% by weight of the composition.

Cosmetically acceptable carriers suitable for skin care compositions according to some embodiments of the present invention include water, emollients, fatty acids, fatty alcohols, thickeners and combinations thereof. The cosmetically acceptable carrier for skin care compositions according to some embodiments of the present invention may be aqueous, anhydrous or an emulsion.

In some embodiments, the cosmetically acceptable carrier for skin care compositions are aqueous, and include water and oil emulsions of the W/O or O/W type or multiple emulsions of the W/O/W or O/W/O variety.

Water, when present in skin care compositions according to some embodiments of the present invention, may be in amounts ranging from 5% to 95% by weight of the skin care composition. Alternatively, the water may be present in amounts ranging from 20% to 70% by weight of the skin care composition. Alternatively, the water may be present from 35% to 60% by weight of the skin care composition. Alternatively, the water may be present from 10% to 95% by weight of the skin care composition. Alternatively, the water may be present from 15% to 95% by weight of the skin care composition. Alternatively, the water may be present from 20% to 95% by weight of the skin care composition. Alternatively, the water may be present from 25% to 95% by weight of the skin care composition. Alternatively, the water may be present from 30% to 95% by weight of the skin care composition. Alternatively, the water may be present from 35% to 95% by weight of the skin care composition. Alternatively, the water may be present from 40% to 95% by weight of the skin care composition. Alternatively, the water may be present from 45% to 95% by weight of the skin care composition. Alternatively, the water may be present from 50% to 95% by weight of the skin care composition. Alternatively, the water may be present from 55% to 95% by weight of the skin care composition. Alternatively, the water may be present from 60% to 95% by weight of the skin care composition. Alternatively, the water may be present from 65% to 95% by weight of the skin care composition. Alternatively, the water may be present from 70% to 95% by weight of the skin care composition. Alternatively, the water may be present from 75% to 95% by weight of the skin care composition. Alternatively, the water may be present from 80% to 95% by weight of the skin care composition. Alternatively, the water may be present from 85% to 95% by weight of the skin care composition. Alternatively, the water may be present from 90% to 95% by weight of the skin care composition.

In some embodiments of a skin care composition of the present invention, the cosmetically acceptable carrier is an emollient material. The emollient material may be in the form of silicone oils, natural or synthetic esters, hydrocarbons, alcohols and fatty acids. Amounts of the emollient material may range from 0.1% to 95% by weight of the skin care composition. Alternatively, the emollient material may range from 1% to 50% by weight of the skin care composition. Alternatively, the emollient material may range from 0.1% to 90% by weight of the skin care composition. Alternatively, the emollient material may range from 0.1% to 85% by weight of the skin care composition. Alternatively, the emollient material may range from 0.1% to 80% by weight of the skin care composition. Alternatively, the emollient material may range from 0.1% to 75% by weight of the skin care composition. Alternatively, the emollient material may range from 0.1% to 70% by weight of the skin care composition. Alternatively, the emollient material may range from 0.1% to 65% by weight of the skin care composition. Alternatively, the emollient material may range from 0.1% to 60% by weight of the skin care composition. Alternatively, the emollient material may range from 0.1% to 55% by weight of the skin care composition. Alternatively, the emollient material may range from 0.5% to 95% by weight of the skin care composition. Alternatively, the emollient material may range from 0.5% to 90% by weight of the skin care composition. Alternatively, the emollient material may range from 0.5% to 85% by weight of the skin care composition. Alternatively, the emollient material may range from 0.5% to 80% by weight of the skin care composition. Alternatively, the emollient material may range from 0.5% to 75% by weight of the skin care composition. Alternatively, the emollient material may range from 0.5% to 70% by weight of the skin care composition. Alternatively, the emollient material may range from 0.5% to 65% by weight of the skin care composition. Alternatively, the emollient material may range from 0.5% to 60% by weight of the skin care composition. Alternatively, the emollient material may range from 0.5% to 50% by weight of the skin care composition.

Silicone oils may be volatile silicone oils, or non-volatile silicone oils. The term "volatile" as used herein refers to those materials which have a measurable vapor pressure at ambient temperature.

Volatile silicone oils suitable for a skin care composition according to some embodiments of the present invention may be cyclic (cyclomethicone) or linear polydimethylsiloxanes containing from 3 to 9 silicon atoms. In one embodiment, the linear polydimethylsiloxanes 5 to 6, silicon atoms.

Non-volatile silicone oils suitable for a skin care composition according to some embodiments of the present invention include polyalkyl siloxanes, polyalkylaryl siloxanes and polyether siloxane copolymers. The non-volatile polyalkyl siloxanes useful herein include, for example, polydimethyl siloxanes with viscosities of from $5 \times 10^{-6}$ to 0.1 $m^2/s$ at 25° C.

In some embodiments, the non-volatile silicone oils suitable for a skin care composition are polydimethyl siloxanes having viscosities from $1 \times 10^{-5}$ to $4 \times 10^{-4}$ $m^2/s$ at 25° C.

Another class of non-volatile silicone oils suitable for a skin care composition according to some embodiments of the present invention are emulsifying and non-emulsifying silicone elastomers, such as, for example, Dimethicone/Vinyl Dimethicone Crosspolymer available as Dow Corning 9040, General Electric SFE 839, and Shin-Etsu KSG-18.

Another class of non-volatile silicone oils suitable for a skin care composition according to some embodiments of the present invention are silicone waxes such as, for example, Silwax WS-L (Dimethicone Copolyol Laurate) may also be useful.

Ester emollients suitable for a skin care composition according to some embodiments of the present invention may include alkyl esters of saturated fatty acids having 10 to 24 carbon atoms. Examples include, but are not limited to, behenyl neopentanoate, isononyl isonanonoate, isopropyl myristate and octyl stearate.

In another example, ester emollients suitable for a skin care composition according to some embodiments of the present invention include ether-esters such as fatty acid esters of ethoxylated saturated fatty alcohols.

In another example, ester emollients suitable for a skin care composition according to some embodiments of the present invention include polyhydric alcohol esters. Examples include, but are not limited to ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

In another example, ester emollients suitable for a skin care composition according to some embodiments of the present invention include wax esters such as, for example, beeswax, spermaceti wax and tribehenin wax.

In another example, ester emollients suitable for a skin care composition according to some embodiments of the present invention include sugar ester of fatty acids such as, for example, sucrose polybehenate and sucrose polycottonseedate.

In some embodiments of skin care compositions according to the present invention, natural ester emollients are based upon mono-, di- and tri-glycerides. Representative glycerides include, but are not limited to, sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof.

In some embodiments of skin care compositions according to the present invention, animal derived emollients include, but are not limited to lanolin oil and lanolin derivatives.

In some embodiments of skin care compositions according to the present invention, amounts of the natural esters range from 0.1% to 20% by weight of the skin care composition. In some embodiments of skin care compositions according to the present invention, amounts of the natural esters range from 0.2% to 20% by weight of the skin care composition. In some embodiments of skin care compositions according to the present invention, amounts of the natural esters range from 0.3% to 20% by weight of the skin care composition. In some embodiments of skin care compositions according to the present invention, amounts of the natural esters range from 0.4% to 20% by weight of the skin care composition. In some embodiments of skin care compositions according to the present invention, amounts of the natural esters range from 0.5% to 20% by weight of the skin care composition. In some embodiments of skin care compositions according to the present invention, amounts of the natural esters range from 1% to 20% by weight of the skin care composition. In some embodiments of skin care compositions according to the present invention, amounts of the natural esters range from 2% to 20% by weight of the skin care composition. In some embodiments of skin care compositions according to the present invention, amounts of the natural esters range from 3% to 20% by weight of the skin care composition. In some embodiments of skin care compositions according to the present invention, amounts of the natural esters range from 4% to 20% by weight of the skin care composition. In some embodiments of skin care compositions according to the present invention, amounts of the natural esters range from 5% to 20% by weight of the skin care composition. In some embodiments of skin care compositions according to the present invention, amounts of the natural esters range from 6% to 20% by weight of the skin care composition. In some embodiments of skin care compositions according to the present invention, amounts of the natural esters range from 7% to 20% by weight of the skin care composition. In some embodiments of skin care compositions according to the present invention, amounts of the natural esters range from 8% to 20% by weight of the skin care composition. In some embodiments of skin care compositions according to the present invention, amounts of the natural esters range from 9% to 20% by weight of the skin care composition. In some embodiments of skin care compositions according to the present invention, amounts of the natural esters range from 10% to 20% by weight of the skin care composition. In some embodiments of skin care compositions according to the present invention, amounts of the natural esters range from 15% to 20% by weight of the skin care composition.

In some embodiments of skin care compositions according to the present invention, suitable hydrocarbons include, but are not limited to, petrolatum, mineral oil, $C_{11}$-$C_{13}$ isoparaffins, polybutenes and especially isohexadecane, available commercially as Permethyl 101 A from Presperse Inc. Fatty acids having from 10 to 30 carbon atoms may also be suitable as cosmetically acceptable carriers for skin care compositions according to some embodiments of the present invention. Illustrative of this category are pelargonic, lauric, myristic, palmitic, stearic, isostearic, oleic, linoleic, linolenic, hydroxystearic and behenic acids and mixtures thereof.

In some embodiments of skin care compositions according to the present invention, the cosmetically acceptable carrier is fatty alcohols having from 10 to 30 carbon atoms. Suitable fatty alcohols include, but are not limited to, stearyl alcohol, lauryl alcohol, myristyl alcohol, oleyl alcohol and cetyl alcohol, or mixtures thereof.

Thickeners can be utilized as part of the cosmetically acceptable carrier of skin care compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for skin care compositions according to the present invention include, but are not limited to, guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®).

Amounts of the thickener may range from 0.0001 to 10%, alternatively from 0.001 to 1%, alternatively from 0.01 to 0.5% by weight of the composition. Emollients that can be used, especially for products intended to be applied to the face, to improve sensory properties include, polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof. Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, alternatively between 1 and 15% by weight of the composition.

In some embodiments of the skin care compositions of the present invention, skin moisturizers, such as, for example, hyaluronic acid and/or its precursor N-acetyl glucosamine are included. N-acetyl glucosamine may be found in shark cartilage or shitake mushrooms and are available commercially from Maypro Industries, Inc (New York). Other moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$alkyl)ammonium salts. In some embodiments, the hydroxypropyl tri($C_1$-$C_3$ alkyl)ammonium salt is 1,2-dihydroxypropyltrimonium chloride, wherein the $C_1$-$C_3$ alkyl is a methyl group. Amounts of the salt may range 0.2% to 30% by weight of the composition. Alternatively, the amount of the salt may range from 0.5 to 20% by weight of the composition. Alternatively, the amount of the salt may range from 1% to 12% by weight of the composition, including all ranges subsumed therein.

In some embodiments, the $C_1$-$C_3$ alkyl constituent on the quatemized ammonium group will be methyl, ethyl, n-propyl, isopropyl or hydroxyethyl and mixtures thereof. In some embodiments, the $C_1$-$C_3$ alkyl constituent on the quatemized ammonium group is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Organic anionic counter ions include, but are not limited to, methosulfate, toluoyl sulfate, acetate, citrate, tartrate, lactate, gluconate, and benzenesulfonate.

In some embodiments of skin care compositions, mosturizers include substituted ureas, such as, for example, hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra(hydroxyethyl) urea; tetra(hydroxypropyl urea; N-methyl, N'-hydroxyethyl urea; N-ethyl-N'-hydroxyethyl urea; N-hydroxypropyl-N'-hydroxyethyl urea and N,N'dimethyl-N-hydroxyethyl urea. Where the term hydroypropyl appears, the meaning is generic for either 3-hydroxy-n-propyl, 2-hydroxy-n-propyl, 3-hydroxy-i-propyl or 2-hydroxy-i-propyl radicals. In some embodiments, the substituted urea is hydroxyethyl urea. The latter is available as a 50% aqueous liquid from the National Starch & Chemical Division of ICI under the trademark HYDROVANCE®.

Amounts of substituted urea that may be used in skin compositions according to some embodiments of the present invention range from 0.01% to 20% by weight of the composition. Alternatively, from 0.5% to 15% by weight of the composition. Alternatively, from 2% to 10% by weight of the composition, and including all ranges subsumed therein.

In some embodiments, a humectant, such as, for example, glycerine is used at least 0.01% to 25% by weight of the composition, alternatively from 0.2% to 20% by weight of the composition, alternatively from 1% to 15% by weight of the composition. In some embodiments, the humectant is included when ammonium salt and substituted urea are used in the skin care composition.

In some embodiments, the skin care composition contains a surfactant. The total concentration of the surfactant when present may range from 0.1% to 90%, alternatively from 0.1% to 80%, alternatively from 0.1% to 70%, alternatively from 0.1% to 60%, alternatively from 0.1% to 50%, alternatively from 0.1% to 40%, alternatively from 0.1% to 30%, alternatively from 0.1% to 20%, alternatively from 0.1% to 10%, alternatively from 1% to 40%, alternatively from 1 to 20% by weight of the composition. The amount of surfactant is dependent on a variety of factors, including, but not limited to, the type of personal care product. The Compounds included in the present invention as exemplified by Compounds 1 through 19, are not considered surfactants and are not included in the amounts of surfactants.

In some embodiments, the surfactant is selected from the group consisting of anionic, nonionic, cationic and amphoteric actives. In some embodiments, nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. In some embodiments, the non-ionic surfactant is selected from the group consisting of alkyl polyglycosides, saccharide fatty amides (e.g. methyl gluconamides) and trialkylamine oxides.

Amphoteric surfactants suitable in skin care compositions according to some embodiments of the present invention include cocoamidopropyl betaine, $C_{12}$-$C_{20}$ trialkyl betaines, sodium lauroamphoacetate, and sodium laurodiamphoacetate.

Anionic surfactants suitable in skin care compositions according to some embodiments of the present invention include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof. Anionic surfactants are irritating to the skin, however, and skin care compositions of the invention are preferably devoid of anionic surfactants, i.e. contain less than 1%, and preferably less than 0.5% of the anionic surfactant.

In some embodiments, the skin care composition of the present invention also includes a rheology modifier. In some embodiments, the rheology modifier is selected from the group consisting of silica such as fumed silica or hydrophilic silicas and clays such as magnesium aluminum silicate, betonites, hectorite, laponite, and mixtures thereof.

In some embodiments, the rheology modifier is in an amount of from 0.01% to 2%, alternatively from 0.02% to 2%, alternatively from 0.03% to 2%, alternatively from 0.04% to 2%, alternatively from 0.05% to 2%, alternatively from 0.06% to 2%, alternatively from 0.07% to 2%, alternatively from 0.08% to 2%, alternatively from 0.09% to 2%, alternatively from 0.1% to 2%, alternatively from 0.15% to 2%, alternatively from 0.2% to 2%, alternatively from 0.25% to 2%, alternatively from 0.5% to 2%, alternatively from 0.1% to 2%, alternatively from 0.05% to 1% by weight of the composition.

In some embodiments, the personal care composition, and especially a skin care composition of the present invention contains sun-screen. The personal care compositions of the present technology surprisingly exhibit SPF and UVAPF values significantly higher than similar compositions that do not include compounds of Formula I. Thus, the personal care compositions of the present technology exhibit enhanced photoprotection properties without needing to increase the sunscreen oil amounts in the composition. The UV-B sunscreen oil may be selected from the class of cinnamic acid, salicylic acid, diphenyl acrylic acid, or derivatives thereof. The UV-B sunscreen oil may include one or more of octyl salicylate, 3,3,5-trimethylcyclohexyl 2-hydroxybenzoate, ethylhexyl salicylate, 2-ethylhexyl 2-cyano-3,3-diphenyl-2-propenoate, or 2-ethylhexyl-4-methoxycinnamate (also known as octyl methoxycinnamate or "OMC"). Such UV-B sunscreen oils are typically commercially available, such as Octisalate™ (octyl salicylate), Homosalate™ (3,3,5-trimethyleyclohexyl 2-hydroxybenzoate), NeoHeliopan™ (a range of organic UV filters including OMC (Neo Heliopan AV™) and ethylhexyl salicylate (Neo Heliopan OS™)), Octocrylene™ and Milestab 3039™ (2-ethylhexyl-2-cyano-3,3-diphenyl-2-propenoate) or Parsol MCX™ (2-ethylhexyl-4-methoxycinnamate). The amount of UV-B sunscreen oil in the personal care composition may be about 0.1 wt % to about 20 wt %, preferably about 0.2 wt % to about 10 wt %, more preferably about 0.5 wt % to about 7 wt %, most preferably about 2 wt % to about 6 wt %.

The personal care composition may further include a UV-B sunscreen that is water-soluble. The water soluble UV-B sunscreen may also include phenylbezimidazole sulfonic acid (also known as ensulizole), 4-aminobenzoic acid (also known as para-aminobenzoic acid or "PABA"), or both.

The personal care composition of any one of the above embodiments may further include about 0.1 wt % to about 10 wt % of a UV-A sunscreen oil. The personal care compositions of the present technology that incorporate a UV-A sunscreen oil exhibit a significantly higher UVAPF when compared to compositions lacking the cyclocarboxylic acid. The UV-A sunscreen oil may include one or more of 4-t-butyl-4'-methoxydibenzoylmethane ("avobenzone"), 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxy-dibenzoylmethane, 2-methyl-5-tert-butyl-4'-methoxy-d benzoylmethane, 2,4-dimethyl-4'-methoxydibenzoylmethane, 2,6-d imehyl-4-tert-butyl-4'methoxy-d ibenzoylmethane, diethylaminohydroxybenzoyl hexyl benzoate, ecamsule, or methyl anthranilate. The amount of UV-A sunscreen oil in the personal care composition may preferably be about 0.5 wt % to about 7 wt %, more preferably about 1 wt % to about 5 wt %.

Additional suitable sunscreen oils suitable for use in the personal care composition include those commercially available from BASF corporation: Uvinul T-150 (Ethylhexyl triazone; a UV-B sunscreen oil), Uvinul A Plus (Diethylamino hydroxybenzoyl hexyl benzoate; a UV-A sunscreen oil), Tinosorb S (bis-ethylhexyloxyphenol methoxyphenyl triazine; a UV-A and UV-B sunscreen oil), Tinosorb M(methylene bisbenzotriazolyl tetramethylbutylphenol; a UV-A and UV-B sunscreen oil). Bisdisulizone disodium may also be included in the personal care composition.

A particularly preferred combination of UV-A and UV-B sunscreen oils is avobenzone and 2-ethylhexyl-4-methoxycinnamate.

In some embodiments, the sunscreen is an inorganic sunscreen. Examples of inorganic sunscreens suitable for use in the skin care composition of the present invention include, but are not limited to, microfine titanium dioxide, zinc oxide, polyethylene and various other polymers. By the term "microfine" is meant particles of average size ranging from 10 to 200 nm, alternatively from 20 to 100 nm. Amounts of the sunscreen when present in a skin care formulation according to some embodiments of the present invention may range from 0.1% to 30%, alternatively from 2% to 20%, alternatively from 4% to 10% by weight of the composition.

In some embodiments, the compound of Formula (1) increases the sun protection factor (SPF) of the personal care composition. In some embodiments, the compound of Formula (1) increases UVA protection factor (UVAPF) of the personal care composition. Without intending to be limited to any particular theory, the increase in UVAPF and SPF can result from an increase in the solubility of a sunscreen in the personal care composition of the present invention. Alternatively, the increase in sun protection factor can result from an increase in the dispersion of a sunscreen in the personal care composition of the present invention.

In some embodiments, the compound of Formula (1) increases the SPF from 20% to 125%. In some embodiments, the compound of Formula (1) increases the SPF from 20% to 120%. In some embodiments, the compound of Formula (1) increases the SPF from 20% to 115%. In some embodiments, the compound of Formula (1) increases the SPF from 20% to 110%. In some embodiments, the compound of Formula (1) increases the SPF from 20% to 105%. In some embodiments, the compound of Formula (1) increases the SPF from 20% to 100%. In some embodiments, the compound of Formula (1) increases the SPF from 20% to 95%. In some embodiments, the compound of Formula (1) increases the SPF from 20% to 90%. In some embodiments, the compound of Formula (1) increases the SPF from 20% to 85%. In some embodiments, the compound of Formula (1) increases the SPF from 20% to 80%. In some embodiments, the compound of Formula (1) increases the SPF from 20% to 75%. In some embodiments, the compound of Formula (1) increases the SPF from 20% to 70%. In some embodiments, the compound of Formula (1) increases the SPF from 20% to 65%. In some embodiments, the compound of Formula (1) increases the SPF from 20% to 60%. In some embodiments, the compound of Formula (1) increases the SPF from 20% to 55%. In some embodiments, the compound of Formula (1) increases the SPF from 20% to 50%. In some embodiments, the compound of Formula (1) increases the SPF from 20% to 45%. In some embodiments, the compound of Formula (1) increases the SPF from 20% to 40%. In some embodiments, the compound of Formula (1) increases the SPF from 20% to 35%. In some embodiments, the compound of Formula (1) increases the SPF from 20% to 30%. In some embodiments, the compound of Formula (1) increases the SPF from 20% to 25%.

The personal care composition of any embodiment described herein preferably includes a skin lightening ingredient. Illustrative skin lightening ingredients include, but are not limited to, placental extract, lactic acid, niacinamide, arbutin, kojic acid, ferulic acid, hydroquinone, resorcinol, resorcinol derivatives (including 4-substituted resorcinols, such as especially 4-hexyl. 4-ethyl, 4-butyl, and/or 4-isopropyl resorcinols), dicarboxylic acids, 12-hydroxystearic acid ("12HSA"), and combinations of any two or more thereof. The skin lightening ingredient preferably includes a tyrosinase inhibitor to complement the melanogenesis inhibition activity of the substituted monoamines, such as kojic acid, hydroquinone and a 4-substituted resorcinol. Dicarboxylic acid skin lightening ingredients include those represented by the formula HOOC—$(C_xH_y)$-COOH where x is 4, 5, 6, 7, 8, 9, 10, 11, 12, 13, 14, 15, 16, 17, 18, 19, or 20, and y is 6, 8, 10, 12, 14, 16, 18, 20, 22, 24, 26, 28, 30, 32, 34, 36, 38, or 40, where such dicarboxylic acids include, but are not limited to, azelaic acid, sebacic acid, oxalic acid, succinic acid, fumaric acid, octadecenedioic acid, salts thereof, and mixtures of any to or more thereof. The amount of skin lightening ingredient may be about 0.1 wt % to about 10 wt %, or any range including and between these two values. For example, the amount of skin lightening ingredient is preferably from about 0.5 wt % to about 2 wt % of the personal care composition. It is further preferred that the skin lightening ingredient include a coactive such as vitamin B3, a vitamin B3 derivative, (e.g., niacinamide, nicotinic acid esters, non-vasodilating esters of nicotinic acid, nicotinyl amino acids, nicotinyl alcohol esters of carboxylic acids, nicotinic acid N-oxide, niacinamide N-oxide) or mixtures of any two or more thereof.

Another preferred cosmetic benefit ingredient is a retinoid. As used herein, "retinoid" includes all natural and/or synthetic analogs of vitamin A, or retinal-like compounds which possess the biological activity of vitamin A in the skin, as well as geometric isomers and stereoisomers of these compounds. The retinoid is preferably retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. Such compounds are well known in the art and are commercially available from a number of sources, e.g., Sigma Chemical Company (St. Louis, Mo.), and Boerhinger Mannheim (Indianapolis, Ind.). Retinoids include those described in U.S. Pat. Nos. 4,677,120, 4,885,311, 5,049,584, 5,124,356, and U.S. Pat. No. Reissue 34,075, as well as tocopheryl-retinoate (the tocopherol ester of retinoic acid), adapalene (6-[3-(1-adamantyl)-4-methoxyphenyl]-2-naphthoic acid), and tazarotene (ethyl 6-[2-(4,4-dimethylthiochroman-6-yl)-ethynyl]nicotinate). Preferred retinoids include retinol, retinyl palmitate, retinyl acetate, retinyl propionate, retinal and combinations of any two or more thereof. The personal care compositions of the present technology may contain a safe and effective amount of the retinoid, such that the personal care composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from 0.005% to 2%, more preferably 0.01% to 2%, retinoid. Retinol is preferably used in about 0.01 wt % to about 0.15 wt %; retinol esters are preferably used in an amount of about 0.01 wt % to about 2 wt %; retinoic acids are preferably used in an amount of about 0.01% to about 0.25%; tocopheryl-retinoate, adapalene, and tazarotene are each preferably used in an amount of about 0.01% to about 2%.

A wide variety of herbal extracts are useful as cosmetic benefiting ingredients. Illustrative herbal extracts include pomegranate, white birch (Betula Alba), green tea, chamomile, licorice, extracts thereof, and combinations of any two or more thereof. The herbal extracts may either be water soluble or water-insoluble, carried in a solvent which respectively is hydrophilic or hydrophobic. Water and ethanol are the preferred extract solvents. The herbal extract may be about 0.000001 wt % to about 10 wt % of the personal care composition, preferably from 0.0001 wt % to about 1 wt %.

Anti-fungal agents suitable for inclusion in personal care compositions are well known to one of skill in the art. Examples include, but are not limited to, climbazole, ketoconazole, fluconazole, clotrimazole, miconazole, econazole, etaconazole, terbinafine, salts of any one or more of these (e.g., hydrochloride salts), zinc pyrithione, selenium disulfide, and combinations of any two or more thereof.

The personal care composition may also include one or more of resveratrol, alpha-lipoic acid, ellagic acid, kinetin, retinoxytrimethylsilane (available from Clariant Corp. under the Silcare 1M-75 trademark), dehydroepiandrosterone (DHEA), and combinations of any two or more thereof. Ceramides (including Ceramide 1, Ceramide 3, Ceramide 3B, Ceramide 6 and Ceramide 7) as well as pseudoceramides may also be included in any embodiment of the personal care composition described herein, but may also be excluded from any embodiment of the personal care composition described herein. Amounts of these materials may range from about 0.000001 wt % to about 10 wt % of the personal care composition, preferably from 0.0001 wt % to about 1 wt %.

Colorants, opacifiers and abrasives may also be included in the personal care composition of the present technology. Each of these substances may range from about 0.05 wt % to about 5 wt %, preferably from about 0.1 wt % to about 3 wt %, of the composition.

The personal care composition may further include about 0.1 wt % to about 8 wt % of a film forming polymer. Such film-forming polymers include, but are not limited to, polyalkyleneoxy terminated polyamides (e.g., INCI name: Polyamide-3, Polyamide-4), polyether polyamides (e.g., INCI name: Polyamide-6), mixed acid terminated polyamides (e.g., INCI name: Polyamide-7), and ester terminated poly(ester-amides) (e.g., INCI name: Polyamide-8). Such film forming polymers may be synthesized or are available commercially, such as under the Sylvaclear™ line of products by Arizona Chemical Company, LLC and the Oleo-Craft™ line of products by Croda International PLC. Film-forming polymers also include, but are not limited to, the INCI named Polyester-5 (e.g., Eastman AQ™ 38S Polymer), PPG-17/IPDI/DMPA Copolymer (e.g., Avalure™ UR 450 Polymer), Acrylates Copolymer (e.g., Avalure™ AC 120 Polymer), and polysaccharides such as Xilogel (tamarin gum), lotus bean gums, tara gum, beta glucan, pullulan, carboxymethyl cellulose, hydroxypropyl cellulose, sodium alginate, potato starch, carrageenan. The film forming polymer may include combinations of any two or more of the polymers recited above. The amount of film forming polymer in the personal care composition may be about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.2 wt %, about 1.4 wt %, about 1.6 wt %, about 1.8 wt %, about 2.0 wt %, about 2.2 wt %, about 2.4 wt %, about 2.6 wt %, about 2.8 wt %, about 3.0 wt %, about 3.2 wt %, about 3.4 wt %, about 3.6 wt %, about 3.8 wt %, about 4.0 wt %, about 4.2 wt %, about 4.4 wt %, about 4.6 wt %, about 4.8 wt %, about 5.0 wt %, about 5.2 wt %, about 5.4 wt %, about 5.6 wt %, about 5.8 wt %, about 6.0 wt %, about 6.2 wt %, about 6.4 wt %, about 6.6 wt %, about 6.8 wt %, about 7.0 wt %, about 7.2 wt %, about 7.4 wt %, about 7.6 wt %, about 7.8 wt %, about 8.0 wt % or any range including and between any two of these values. Preferable amounts of film forming polymer are about 1 wt % to about 3 wt %. Further ingredients useful in skin care compositions herein may be selected from any and all: skin conditioning agents, skin feel mildness agents, suspending agents, auxiliary thickening agents, viscosity control agents, dispersants, solubilizing/clarifying agents, stabilizers, opacifiers/pearlescent agents, chelating/sequestering agents, hydrotropes, bactericides/fungicides, antioxidants, pH control agents, buffering agents, colorants and perfumes/fragrances, water, other optional ingredients (auxiliary agents) and the like. The compositions of the present invention can also be optionally, incorporated into a water insoluble substrate for application to the skin such as in the form of a treated wipe.

Preservatives can be incorporated into the personal care compositions according to some embodiments of the present invention to protect against the growth of potentially harmful microorganisms. Suitable preservatives for personal care compositions according to some embodiments of the present invention include, but are not limited to alkyl esters of para-hydroxybenzoic acid. Other suitable preservatives include hydantoin derivatives, propionate salts, and a variety of quaternary ammonium compounds.

Other suitable preservatives include 1,2-alkane diols (e.g. 1,2-octane diol), phenoxyethanol, methyl paraben, propyl paraben, imidazolidinyl urea, sodium dehydroacetate and benzyl alcohol.

The preservatives should be selected having regard for the use of the composition and possible incompatibilities between the preservatives and other ingredients in the emulsion. Preservatives can be included in the personal care compositions of the present invention in amounts ranging from 0.01% to 2% by weight of the composition. Alternatively, preservatives can be included in the personal care compositions of the present invention in amounts ranging from 0.02% to 2% by weight of the composition. Alternatively, preservatives can be included in the personal care compositions of the present invention in amounts ranging from 0.03% to 2% by weight of the composition. Alternatively, preservatives can be included in the personal care compositions of the present invention in amounts ranging from 0.04% to 2% by weight of the composition. Alternatively, preservatives can be included in the personal care compositions of the present invention in amounts ranging from 0.05% to 2% by weight of the composition. Alternatively, preservatives can be included in the personal care compositions of the present invention in amounts ranging from 0.15% to 2% by weight of the composition. Alternatively, preservatives can be included in the personal care compositions of the present invention in amounts ranging from 0.2% to 2% by weight of the composition. Alternatively, preservatives can be included in the personal care compositions of the present invention in amounts ranging from 0.5% to 2% by weight of the composition. Alternatively, preservatives can be included in the personal care compositions of the present invention in amounts ranging from 1% to 2% by weight of the composition. Alternatively, preservatives can be included in the personal care compositions of the present invention in amounts ranging from 1.5% to 2% by weight of the composition.

In some embodiments, the personal care compositions of the present invention include vitamins. Illustrative vitamins are Vitamin A (retinol), Vitamin B2, Vitamin B3 (niacinamide), Vitamin B6, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. In some embodiments, the Vitamin B6 derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001% to 10%, alternatively from 0.001% to 10%, alternatively from 0.01% to 10%, alternatively from 0.1% to 10%, alternatively from 1% to 10%, alternatively from 0.01% to 1%, alternatively from 0.1% to 0.5% by weight of the composition.

In some embodiments, the personal care compositions of the present invention include an enzyme such as, for example oxidases, proteases, lipases and combinations thereof. In some embodiments, the personal care compositions of the present invention includes superoxide dismutase, commercially available as Biocell SOD from the Brooks Company, USA.

In some embodiments, the personal care compositions of the present invention include desquamation promoters.

In some embodiments, the personal care compositions of the present invention include desquamation promoters at a concentration from 0.01% to 15% by weight of the composition. In some embodiments, the personal care compositions of the present invention include desquamation promoters at a concentration from 0.05% to 15% by weight of the composition. In some embodiments, the personal care compositions of the present invention include desquamation promoters at a concentration from 0.1% to 15% by weight of the composition. In some embodiments, the personal care compositions of the present invention include desquamation promoters at a concentration from 0.5% to 15% by weight of the composition. In some embodiments, the personal care compositions of the present invention include desquamation promoters at a concentration from 1% to 15% by weight of the composition. In some embodiments, the personal care compositions of the present invention include desquamation promoters at a concentration from 5% to 15% by weight of the composition. In some embodiments, the personal care compositions of the present invention include desquamation promoters at a concentration from 10% to 15% by weight of the composition.

Illustrative desquamation promoters include monocarboxylic acids. Monocarboxylic acids may be substituted or unsubstituted with a carbon chain length of up to 16. In some embodiments, the carboxylic acids are the alpha-hydroxycarboxylic acids, beta-hydroxycarboxylic or polyhydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids include glycolic, lactic malic and tartaric acids. In some embodiments, the salt is ammonium lactate.

In some embodiments, the beta-hydroxycarboxylic acid is salicylic acid. In some embodiments, the phenolic acids include ferulic acid, salicylic acid, kojic acid and their salts.

In some embodiments, the at least one additional component may be present from 0.000001% to 10%, alternatively from 0.00001% to 10%, alternatively from 0.0001% to 10%, alternatively from 0.001% to 10%, alternatively from 0.01% to 10%, alternatively from 0.1% to 10%, alternatively from 0.0001% to 1% by weight of the composition. Colorants, opacifiers or abrasives may also be included in compositions of the present invention.

The colorants, opacifiers or abrasives may be included at a concentration from 0.05% to 5%, alternatively between 0.1% and 3% by weight of the composition.

In some embodiments, the personal care product of the present invention may also include a pepdtide, such as, for example, the commercially available pentapeptide derivative—Matrixyl™, which is commercially available from Sederma, France. In another example, in some embodiments, the personal care product of the present invention may also include Carnosine.

Form of Skin Care Compositions: In some embodiments, the skin care compositions of the present invention are non-solid. As used herein, the term "non-solid" means that the viscosity of the compositions, e.g. as measured using a Brookfield DV-I+viscometer (20 RPM, RV6, 30 seconds, 20° C.). In some embodiments, the viscosity is in the range of from 1 Pas to 500 Pas, alternatively from 1 Pas to 200 Pas, alternatively from 2 Pas to 100 Pas, alternatively from 3 Pas to 50 Pas, at 20° C.

In some embodiments, the skin care compositions of the invention are leave-on compositions, wherein the skin care compositions are intended to be applied to, and remain on the skin. Leave-on compositions are to be distinguished from compositions which are applied to the skin and subsequently removed, either by washing, rinsing, wiping, or the like either soon after or during the application of the product. Surfactants typically used for rinse-off compositions have physico-chemical properties giving them the ability to generate foam/lather in-use with ease of rinse; they can consist of mixtures of anionic, cationic, amphoteric, and nonionic surfactants.

In some embodiments, anionic surfactants are present in the leave-on skin care composition in an amount of at most 5% by weight of the composition, alternatively from 0.01% to 4% by weight of the composition, alternatively from 0.01% to 3% by weight of the composition, alternatively from 0.01% to 2% by weight of the composition, alternatively substantially absent (less than 1%, or less than 0.1%, or less than 0.01%). In some embodiments, the total level of surfactant in the skin care compositions is no more than 10%, alternatively below 8%, alternatively at most 5%.

In some embodiments, the skin care compositions of the present invention are in the form of emulsions, which may be oil-in-water, or water-in-oil. In some embodiments, the skin care compositions are oil-in-water emulsions.

Another format is a cream, including one which has a vanishing cream base. Vanishing cream base is one which comprises 5 to 40% fatty acid and 0.1 to 20% soap. In some embodiments, in such creams, the fatty acid is substantially a mixture of stearic acid and palmitic acid and the soap is the potassium salt of the fatty acid mixture, although other counterions and mixtures thereof can be used. The fatty acid in vanishing cream base is often prepared using hystric acid which is substantially (generally 90 to 95%) a mixture of stearic acid and palmitic acid. A typical hystric acid comprises 52-55% palmitic acid and 45-48% stearic acid of the total palmitic-stearic mixture. Thus, inclusion of hystric acid and its soap to prepare the vanishing cream base is within the scope of the present invention. In some embodiments, the skin care composition comprises higher than 7%, or higher than 10%, or higher than 12% fatty acid.

In some embodiments, in addition to containing a compound of Formula (1), the personal care composition is formulated as a shampoo. In some embodiments, the personal care compositions of the present invention are formulated as a deodorant. In some embodiments, in addition to containing a compound of Formula (1), the personal care composition is formulated as a deodorant according to the formulations described in U.S. Pat. No. 7,282,471 B2. In some embodiments, the personal care compositions of the present invention are formulated as an antiperspirant. In some embodiments, in addition to containing a compound of Formula (1), the personal care composition is formulated as an antiperspirant according to the formulations described in U.S. Pat. No. 7,282,471 B2.

In some embodiments, the personal care compositions of the present invention are formulated as a single use personal care towelette product. In some embodiments, in addition to containing a compound of Formula (1), the personal care composition is formulated as a single use personal care towelette product according to the formulations described in U.S. Pat. No. 7,282,471 B2.

In some embodiments, the personal care compositions of the present invention are formulated as a soap bar. In some embodiments, in addition to containing a compound of Formula (1), the personal care composition is formulated as a soap bar according to the formulations described in U.S. Pat. No. 7,282,471 B2.

Methods of Making Skin Care Compositions According to Some Embodiments of the Present Invention In some embodiments, skin care compositions according to the present invention can be made by:
a. mixing all water soluble ingredients including preservatives, thickening polymer, optionally glycerine, and water;
b. heating the mixture to a temperature of 70-90° C.;
c. mixing all the oil soluble ingredients and the compound of formula (1) to a temperature of 70-90° C.;
d. adding the mixed oil soluble ingredients to the heated mixture of water soluble ingredients, and mixing via agitation, maintaining the mixture at a temperature of 70-90° C.; and
e. cooling the mixture to room temperature, whilst mixing.

In some embodiments, nicotinamide is added to the mixture of step (d), at a temperature of 45° C., followed by addition of fragrance and phenoxyethanol at 40° C.

Method of Using the Skin Care Compositions According to Some Embodiments of the Present Invention In some embodiments, the skin care composition is topically applied to human skin. In some embodiments, the skin care composition provides at least one benefit, selected from the group consisting of: skin conditioning, skin smoothening, reduction of wrinkled or aged skin, reduction of inflammation of the skin, reduction of itch, reduction of age spots, an reduction of sun burn, and lightening of the skin.

In some embodiments, a small quantity of the skin care composition, for example from 1 to 5 ml, is applied to exposed area of the skin, from a suitable container or applicator and, if necessary, it is then spread over and/or rubbed into the skin using the hand or fingers or a suitable device.

Reference is now made to the following examples, which together with the above descriptions illustrate some embodiments of the invention in a non-limiting fashion.

EXAMPLES

Example 1: Synthesis of the Compounds According to Some Embodiments of the Present Invention The general method for synthesizing compounds according to some embodiments of the present invention is as follows:

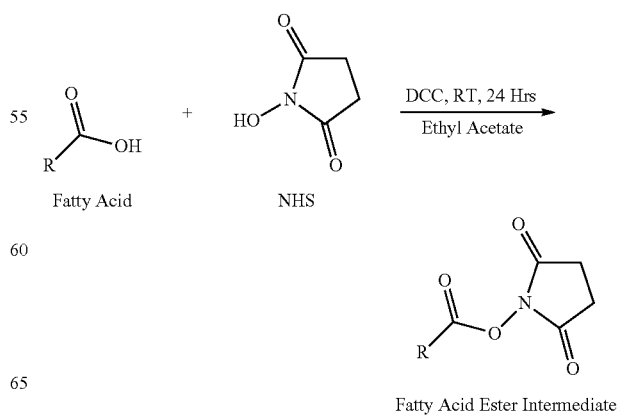

Fatty Acid Ester Intermediate

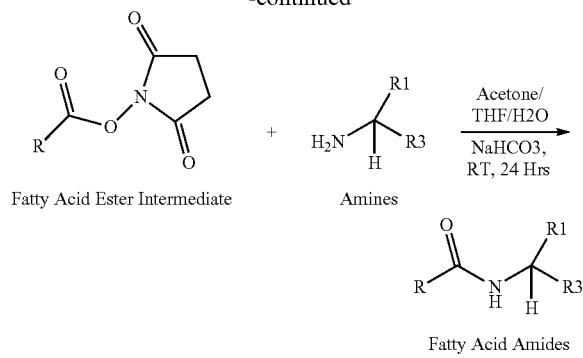

Typically, compounds were synthesized by reacting a fatty acid with N-hydroxysuccinimide (NHS) in the presence of N,N' dicyclohexylcarbodiimide (DCC) in dry ethyl acetate to give the N-hydroxysuccinimide ester of fatty acid intermediate. Reaction of the intermediate with an amine in aqueous acetone/THF/NaHCO₃ gave the corresponding reaction product fatty acid amide in 50-90% yield.

Synthesis of Compound 1: In a one neck 500 ml round bottom flask with magnetic stirrer, dissolved CLA (10 g, 1 eq.) and N-hydroxysuccinimide (4.11 g, 1 eq.) in dry ethyl acetate (150 ml) (I). DCC (7.36 g, 1 eq.) dissolved in ethyl acetate (85 ml). The DCC solution was added slowly with stirring to (I). The reaction mixture was let stirred at room temperature (RT) for 24 hours. The reaction was then vacuum filtered to remove the by-product N,N' dicyclohexylurea as white solid. The filtrate was removed ethyl acetate under rotavap to give clear viscous liquid product (14 g, N-hydroxysuccinimide ester of CLA) which solidified after standing at room temperature (RT).

In a 2 necks 250 ml round bottom flask with magnetic stirrer, condenser, glycine (0.6 g, 1 eq.) and NaHCO3 (1.34 g, 2 eq.) dissolved in water (40 ml). N-hydroxysuccinimide ester of CLA (3 g, 1 eq.) dissolved in acetone/THF (30 ml, 10 ml) was added to the above glycine/NaHCO3 aqueous solution. The reaction solution was let stir at RT for 24 hours. The solution was then added water (200 ml) and acidified with concentrated sulfuric acid to pH-2. The acidified solution mixture was cooled in ice bath. The white precipitate was collected by vacuum filtration. The product was washed with water, air dried follow by dried in P2O5 oven, yield 2.2 g as white solid (82%). The product conjugated linoleyl glycinate acid was confirmed by NMR and MS.

Example 2: FAAH, CB1, and CB2 Inhibition by the Compounds According to Some Embodiments of the Present Invention The ability of the compounds according to some embodiments of the present invention to inhibit FAAH was determined according to the methods disclosed a commercially available kit from Cayman Chemicals (Cayman Cat. No. 10005196). The kit utilizes recombinant human FAAH enzyme which hydrolyzes AMC-arachidonoyl amide resulting in the release of the fluorescent product, 7-amino-4-methylcoumarin (AMC). The fluorophore was detected via fluorescence, using an excitation wavelength of 340-360 nm and an emission wavelength of 450-465 nm. The assay was followed as described in the kit manual, which can be found on the webpage of Cayman Chemicals.

The ability of the compounds according to some embodiments of the present invention to inhibit a radiolabeled cannabinoid ligand, CP-55,940, [Side chain-2,3,4(N)-3H(N)]-(Perkin-Elmer Cat. # NET1051) to either the human CB1 receptor or CB2 receptor was determined according to the manufacturer's instructions in the commercially available membrane preparations from Perkin Elmer (Cat Nos. RBHCB1M400UA and RBXCB2M400UA). Briefly, pretreatment of the glass fiber membrane of a Matrix 96 well GFC filtration microtiter plate was done in order to help reduce non-specific binding of the radioligand to the GFC membrane. This was done by adding 150 µl of 0.5% polyethylimine (PEI) to each well and letting this remain in the plate for at least 4 hours before using it to terminate the binding reaction. The actual binding reaction was performed in a polypropylene (PP) round bottom 96-well microtiter plate. Briefly, 55 µl of assay buffer (50 mM TRIS pH7.4, 2.5 mM EGTA, 5 mM $MgCl_2$, 120 mM NaCl, 0.1% Fatty acid free BSA) was added to each well, followed by 20 µl of a 0.4 mg/ml CB1 or CB2 membrane suspension (8 µg membrane per well). To initiate the reaction, 20 µl of 5 nM $^3$H CP-55,940 (1 nM final concentration) was added to each well. Nonspecific binding was defined in the presence of 20 µM unlabeled WIN 55212 (Sigma cat. W-102). ACEA was routinely used as a positive control for both assays. The plate was shaken on an orbital plate shaker and the binding reaction proceeded until equilibrium was reached after 3 hours at room temperature. Using a Multiscreen vacuum manifold, the PEI was filtered through the GFC filter plate. The binding reaction in the PP plate was mixed by aspirating the reaction contents of each well and dispensing back into the plate. This was repeated 4 times and then 75 µl of the reaction mixture was transferred to the GFC plate. This procedure could be done row by row with the use of a multichannel pipette, or all at once if using automation. Once the entire content of the PP plate was transferred to the GFC plate, the binding reactions were terminated by filtering thru the GFC plate. The filter plate was then washed by adding 100 µl ice-cold wash buffer 50 mM TRIS pH 7.4, 2.5 mM EGTA, 5 mM $MgCl_2$, 120 mM NaCl, 2% Fatty acid free BSA) to each well and filtering through. This was repeated 8 times, after which the filter mat was allowed to dry. Once the filter mat was dry, 50 µl of Microscint scintillation cocktail was added to each well, allowed to sit for 15-20 min, and the plate read on a Microbeta2 scintillation counter.

The lower the $IC_{50}$ value, the higher the binding.

The results that were obtained for the inhibition studies are shown in Table 1.

TABLE 1

| Compound No. | FAAH $IC_{50}$ (µM) | CB1 $IC_{50}$ (µM) | CB2 $IC_{50}$ (µM) |
| --- | --- | --- | --- |
| 1 | 2.6 | No binding | No binding |
| 2 | 2.6 | No binding | No binding |
| 3 | 2.8 | 22 | 26 |
| 4 | 2.8 | 22 | 26 |
| 5 | 3.5 | No binding | No binding |
| 6 | 3.5 | No binding | No binding |
| 7 | 11 | No binding | No binding |
| 8 | 11 | No binding | No binding |
| 9 | 13 | 47 | 38 |
| 10 | 13 | 47 | 38 |
| 11 | No binding | No binding | No binding |
| 12 | 42 | No binding | No binding |
| 13 | Not measured | Not measured | Not measured |
| 14 | 26 | No binding | No binding |
| 15 | Not measured | Not measured | Not measured |
| 16 | Not measured | Not measured | Not measured |

TABLE 1-continued

| Compound No. | FAAH IC$_{50}$ (μM) | CB1 IC$_{50}$ (μM) | CB2 IC$_{50}$ (μM) |
|---|---|---|---|
| 17 | 40 | No binding | No binding |
| 18 | 46 | No binding | No binding |
| 19 | Not measured | Not measured | Not measured |

Compounds 1-6 were conjugated linoleic acid amide derivatives, and inhibited FAAH enzyme activity with IC$_{50}$ values in the 2 to 3 μM range. Compounds 7-10 were conjugated linoleic acid amide derivatives, and inhibited FAAH enzyme activity with IC$_{50}$ values in the 10-20 μM range. Compounds 3, 4, 9, and 10 also demonstrated binding inhibition activities in the CB1/CB2 receptor binding assays with IC$_{50}$ values in the 20-40 μM ranges.

The ricinoleic acid amide derivative Compounds 12 and 14 had IC$_{50}$ values for FAAH enzyme inhibition in the 20 to 40 μM ranges, but had no binding activities for CB1 and CB2. The 12-hydroxystearic acid amide derivative compounds 17 and 18 had IC$_{50}$ values for FAAH enzyme inhibition in the 20 to 40 μM ranges, but had no binding activities for CB1 and CB2.

Several of the more potent compounds were selected for further testing. In particular, the Compound 5 and Compound 14 demonstrated good inhibition of FAAH, with IC$_{50}$ values of 3.5 and 26 μM respectively.

Example 3: Determination of Skin Irritation of the Compounds According to Some Embodiments of the Present Invention The irritation potential of the compounds of the present invention was measured by the Zein solubility test method, as follows:

Zein measurement is initiated by adding 0.5 g Zein powder into 10 ml surfactant solutions (at 2 wt %) to yield the surfactant-Zein-water mixtures. The mixtures are then vortex mixed for 15 minutes and let standing for 30 minutes to reach the solubility equilibrium, centrifuged at 3000 rpms for 20 minutes to isolate the undissolved Zein, rinsed with Milli-Q water to eliminate the surfactant residues, and dried in a vacuum oven at 60° C. for at least 48 hours to remove the excess water.

$$\% \text{ zein dissolved} = \frac{0.5 \text{ g} - \text{wt. of undissolved zein (g)}}{0.5 \text{ g}} \times 100$$

The results that were obtained are shown in Table 2. The greater the Zein solubility, when expressed as a percentage, the more irritating the compound. The compounds tested (compounds 1, 5, 12, 14, 17, and 18) were less irritating than control compounds (SLG, or coco glycinate). Compounds 17 and 18 demonstrated a Zein solubility in the 15% to 20% range. Compounds 1 and 14 demonstrated a Zein solubility in the 20% to 25% range. Compounds 5 and 12 demonstrated a Zein solubility in the 30% to 35% range.

TABLE 2

| 2% total Surfactant and compound within the invention in water Compound name | SLG 20% (g) | co-surfactant (mg) | Zein solubilty (%) |
|---|---|---|---|
| Sodium lauroyl glycinate (SLG), control | 1 | 0 | 74 |
| Sodium lauroyl glycinate (SLG), control | 1 | 0 | 79.3 |
| coco glycinate (control) | 1 | 0 | 77.2 |
| coco glycinate (control) | 1 | 0 | 80.6 |
| Compound 1 | 0.7 | 60 | 25 |
| Compound 1 | 0.7 | 60 | 23 |
| Compound 5 | 0.7 | 60 | 30.7 |
| Compound 5 | 0.7 | 60 | 29.5 |
| Compound 12 | 0.7 | 60 | 31.8 |
| Compound 12 | 0.7 | 60 | 35 |
| Compound 14 | 0.7 | 60 | 23 |
| Compound 14 | 0.7 | 60 | 21 |
| Compound 17 | 0.7 | 60 | 19 |
| Compound 17 | 0.7 | 60 | 15 |
| Compound 18 | 0.7 | 60 | 17.8 |
| Compound 18 | 0.7 | 60 | 15 |

Example 4: Determination of the Effect of Compounds According to Some Embodiments of the Present Invention on the Solubility and/or Dispersion of Organic Sunscreen The ability of the compounds of the present invention to increase the UVAPF and SPF of a composition was determined by measuring the SPF of a composition containing the sunscreen avobenzone and a compound of the present invention, compared to a control composition.

In vitro SPF measurement was performed using an Optometric 290S SPF meter. Personal care compositions were each applied at a dosage of 2 mg/cm$^2$ on a PMMA (polymethylmethacrylate) plate or a glass plate (7 cm×7 cm) and allowed to air dry for 30 minutes at 22° C. The average SPF value was obtained from 6 SPF readings per plate. Two duplicated runs, the standard deviation from the average was ±2 SPF units. The % increase of in vitro SPF versus control is calculated as follows: [(measured SPF for selected formulation−measured SPF of control)/measured SPF of control]*100%.

A single Optometric 290S SPF meter measurement gave both SPF and UVAPF values The % increase of in vitro UVAPF versus control is calculated as follows: [(measured UVAPF for selected formulation−measured UVAPF of control)/measured UVAPF of control]*100%.

Personal care compositions according to the present technology were compared to a control composition that did not incorporate a compound of Formula I included in the present technology.

Control Composition (Vanishing Cream)

| Component | Wt % |
|---|---|
| Stearic Acid | 17 wt % |
| Cetyl Alcohol | 0.53 wt % |
| Methyl Paraben | 0.2 wt % |
| Glycerin | 1.0 wt % |

-continued

| Component | Wt % |
|---|---|
| Potassium Hydroxide ( KOH, 50%) | 0.96 wt % |
| Disodium EDTA | 0.04 wt % |
| Dimethicone | 0.5 wt % |
| Propyl Paraben | 0.1 wt % |
| Isopropyl Myristate | 0.75 wt % |
| 2-ethylhexyl-4-methoxycinnamate (OMC) | 4.0 wt % |
| Avobenzone | 1.5 wt % |
| Niacinamide | 1.25 wt % |
| Phenoxyethanol | 0.4 wt % |
| DI Water | q.s |

The results that were obtained are shown in Table 3.

TABLE 3

|  | SPF | UVAPF | % increase SPF over control | % increase SPF over control average | % increase UVAPF over control | % increase UVAPF over control average |
|---|---|---|---|---|---|---|
| Control | 20.2 | 10.5 |  |  |  |  |
| Control | 20 | 11 |  |  |  |  |
| 1.5% Compound 1 | 40.5 | 23.1 | 102.5 |  | 120.00 |  |
| 1.5% Compound 1 | 38.1 | 21.6 | 90.5 | 96.5 | 96.36 | 108.18 |
| 1.5% Compound 5 | 31.3 | 13.7 | 56.5 |  | 30.48 |  |
| 1.5% Compound 5 | 34.8 | 15.5 | 74 | 65.25 | 40.91 | 35.69 |
| 1.5% Compound 12 | 40.3 | 21.6 | 101.5 |  | 105.71 |  |
| 1.5% Compound 12 | 44.3 | 24.1 | 121.5 | 111.5 | 119.09 | 112.40 |
| 1.5% Compound 14 | 33.6 | 19.2 | 68 |  | 82.86 |  |
| 1.5% Compound 14 | 33.6 | 19.2 | 68 | 68 | 74.55 | 78.70 |
| 1.5% Compound 17 | 29.3 | 14.8 | 46.5 |  | 40.95 |  |
| 1.5% Compound 17 | 30.1 | 15.3 | 50.5 | 48.5 | 39.09 | 40.02 |
| 1.5% Compound 18 | 26.6 | 13.7 | 33 |  | 30.48 |  |
| 1.5% Compound 18 | 27.8 | 14.3 | 39 | 36 | 30.00 | 30.24 |

All compounds tested increased the SPF and UVAPF as determined by measuring the SPF and UVAPF of a composition containing the sunscreen avobenzone and a compound of the present invention, compared to a control composition. Compound 12 demonstrated the largest increase in SPF, of 111.5% over control and UVAPF over 112.4%. The conjugated linoleic acid amide derivative compounds 1 and 5 demonstrated an increase in SPF over control of 95.5% and 65.25% respectively. The conjugated linoleic acid amide derivative compounds 1 and 5 demonstrated an increase in UVAPF over control of 108.18% and 39.65% respectively. The ricinoleic acid amide derivative compounds 12 and 14 demonstrated an increase in SPF over control of 111.5% and 68% respectively. The ricinoleic acid amide derivative compounds 12 and 14 demonstrated an increase in UVAPF over control of 112.4% and 78.7% respectively. The 12-hydroxystearic acid amide derivative compounds 17 and 18 demonstrated an increase in SPF over control of 48.5% and 36% respectively. The 12-hydroxystearic acid amide derivative compounds 17 and 18 demonstrated an increase in UVAPF over control of 40% and 30.24% respectively.

Example 5: Determination of the Effect of Compounds According to Some Embodiments of the Present Invention on the Solubility of 12 HSA The ability of the compounds of the present invention to increase the solubility of 12 HSA was determined. The results are shown in Table 4. The observations range from visible precipitates (ppt), indicating insoluble 12 HSA, through an opaque solution, and a translucent solution, to a clear solution, indicating an increase in solubility of 12 HSA.

TABLE 4

| % Tween 60 | % Tween 20 | % 12-HSA | % Compound | Observation | Compound No. |
|---|---|---|---|---|---|
|  | 58.33 | 41.67 | 0 | opaque, precipitate |  |
|  | 33.33 | 41.67 | 25.00 | translucent | Compound 5 |
| 58.33 |  | 41.67 | 0 | opaque, precipitate |  |
|  | 40 | 30 | 10 | translucent | Compound 5 |
|  | 41.18 | 29.41 | 29.41 | translucent | Compound 14 |
|  | 41.18 | 29.41 | 29.41 | translucent | Compound 12 |
|  | 48.28 | 34.48 | 17.24 | translucent | Compound 5 |
| 48.39 |  | 48.39 | 3.23 | translucent | Compound 18 |

TABLE 4-continued

| % Tween 60 | % Tween 20 | % 12-HSA | % Compound | Observation | Compound No. |
|---|---|---|---|---|---|
|  | 40.00 | 40 | 20 | translucent | Compound 5 |
| 48.28 |  | 34.48 | 17.24 | translucent | Compound 5 |
| 41.18 |  | 29.41 | 29.41 | translucent | Compound 14 |
| 41.18 |  | 29.41 | 29.41 | translucent | Compound 12 |
|  | 48.28 | 34.48 | 17.24 | translucent | Compound 3 |
| 41.18 |  | 29.41 | 29.41 | translucent/clear | Compound 11 |
| 41.18 |  | 29.41 | 29.41 | translucent/clear | Compound 1 |
| 41.18 |  | 29.41 | 29.41 | translucent | Compound 15 |
| 41.18 |  | 29.41 | 29.41 | translucent | Compound 13 |
| 41.67 |  | 41.67 | 16.67 | translucent | Compound 11 |
| 41.67 |  | 41.67 | 16.67 | translucent | Compound 1 |
| 41.67 |  | 41.67 | 16.67 | translucent | Compound 15 |
| 50.00 |  | 35.71 | 14.29 | translucent | Compound 19 |
| 70 |  | 30 | 0 | opaque |  |
| 45.16 |  | 38.71 | 16.13 | translucent | Compound 16 |

All compounds tested were able to increase the solubility of 12 HSA.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Although the various aspects of the invention have been illustrated above by reference to examples and preferred embodiments, it will be appreciated that the scope of the invention is defined not by the foregoing description but by the following claims properly construed under principles of patent law. While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A personal care composition, comprising:
   a. a compound of Formula (1) at a concentration from 0.0001 wt % to 20 wt % of the composition;

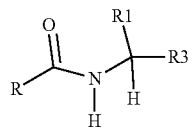

Formula (1)

wherein R is selected from the group consisting of $C_{15}$-$C_{23}$ conjugated dienes, $C_{15}$-$C_{23}$ hydroxylated mono unsaturated alkenes, and $C_{15}$-$C_{23}$ hydroxylated alkanes;

wherein R1 is selected from the group consisting of H, $C_1$-$C_4$ alkyl, —$CH_2OH$, —$CH_2(CH_3)$—OH, —$[CH_2]_4$—$NH_2$, —$CH_2$—$CO_2H$, —$[CH_2]_2$—$CO_2H$,

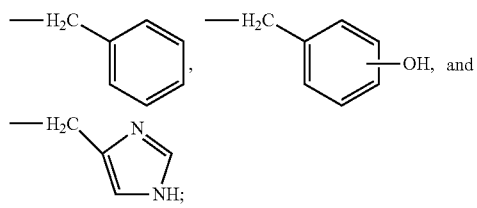

wherein R3 is —$CO_2H$; —$CH_2CO_2H$; —$CH_2CH_2CO_2H$; and b. a cosmetically acceptable carrier;

the composition further comprising an organic sunscreen with the proviso that when $R^3$ is —$CO_2H$, R is a $C_{15}$ to $C_{23}$ hydroxylated alkane.

2. The composition of claim 1, wherein the compound of Formula (1) is an anti-inflammatory agent.

3. The composition of claim 1, wherein the compound of Formula (1) is an anti-itch agent.

4. The composition of claim 1, wherein the compound of Formula (1) inhibits fatty acid amide hydrolase.

5. The composition of claim 1, wherein the compound of Formula (1) comprises a conjugated linoleic acid amide derivative, or a mixture of conjugated linoleic acid derivative, a ricinoleic acid amide derivative, and/or a 12-hydroxystearic acid amide derivative.

6. The composition of claim 5, wherein the conjugated linoleic acid amide derivative is selected from the group consisting of:

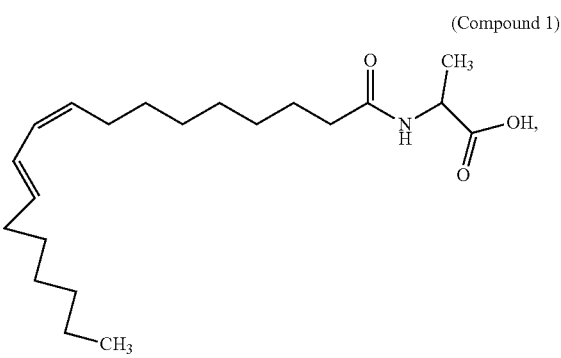
(Compound 1)

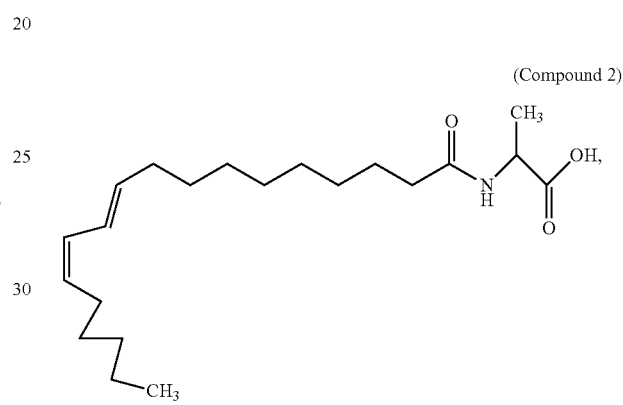
(Compound 2)

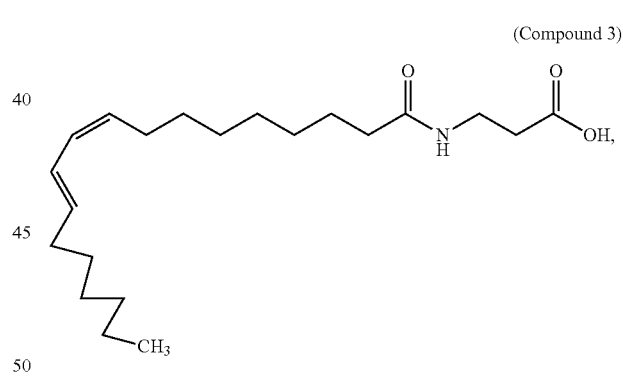
(Compound 3)

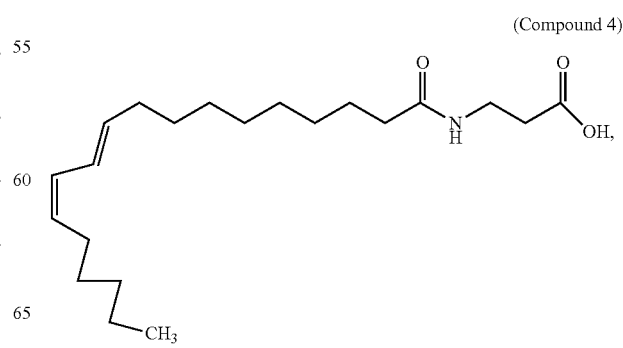
(Compound 4)

(Compound 5)
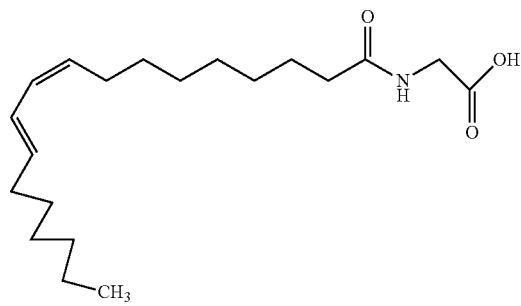
(Compound 6)
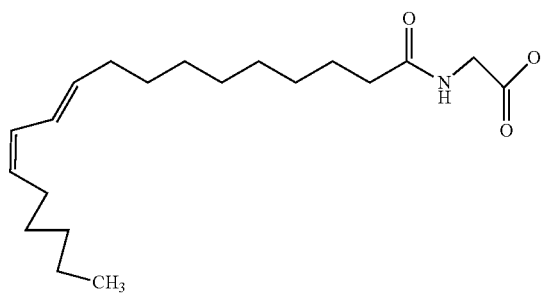
(Compound 7)
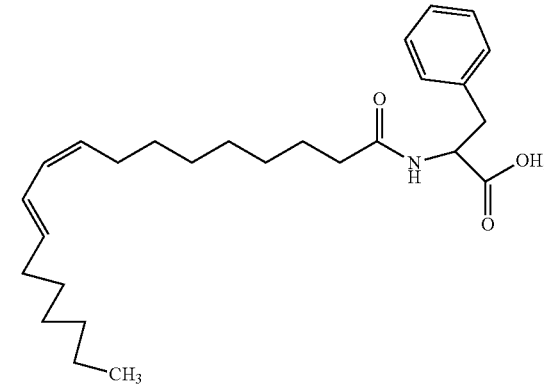
(Compound 8)
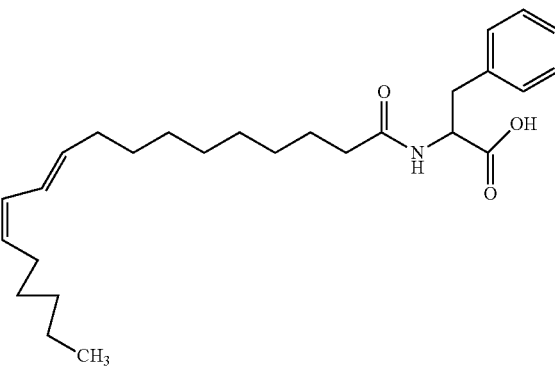
(Compound 9)
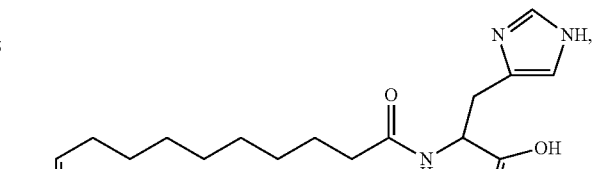
(Compound 10)
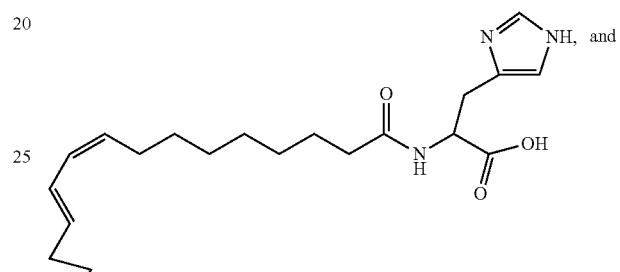
(Compound 11)
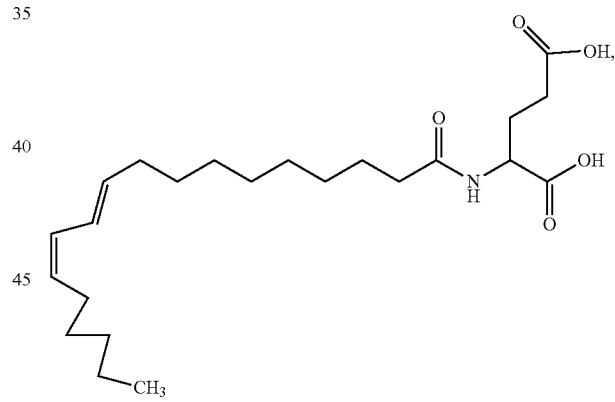
and mixtures thereof.
7. The composition of claim 5, wherein the ricinoleic acid amide derivative is selected from the group consisting of:
(Compound 12)
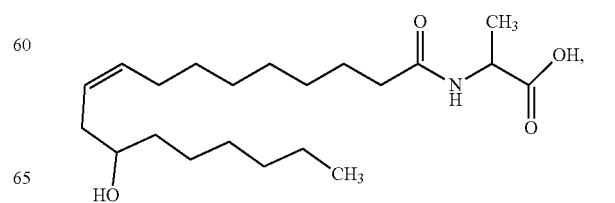

(Compound 13)

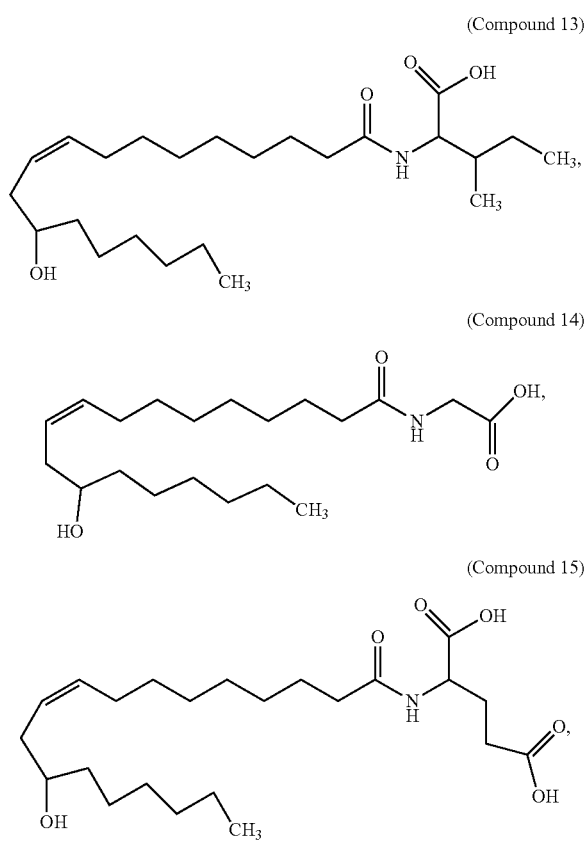

(Compound 14)

(Compound 15)

and mixtures thereof.

8. The composition of claim 5, wherein 12-hydroxystearic acid amide derivative is selected from the group consisting of:

(Compound 16)

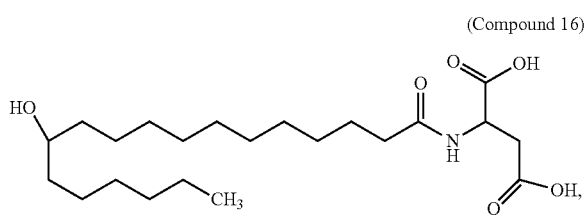

(Compound 17)

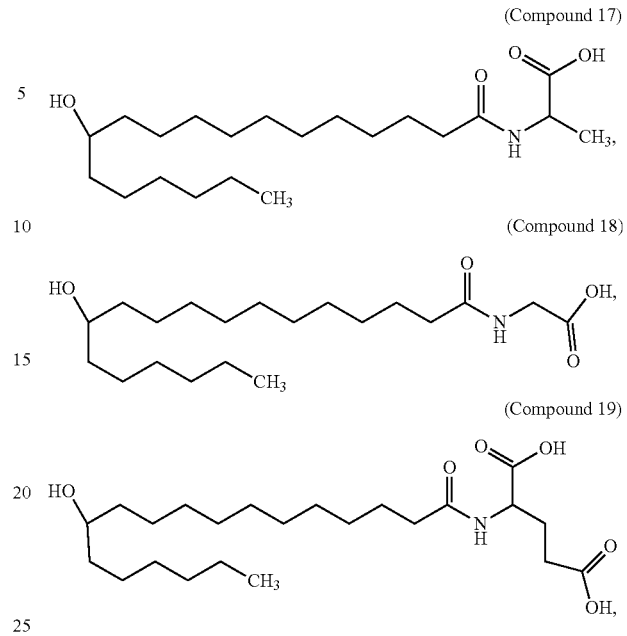

(Compound 18)

(Compound 19)

and mixtures thereof.

9. The composition of claim 1, wherein the personal care composition is a leave-on composition.

10. The composition of claim 1 wherein the organic sunscreen is selected from the group consisting of ethylhexyl p-methoxycinnamate, avobenzone, octylsalicylate, tetraphthalylidene dicamphor sulfonic acid, benzophenone-4, benzophenone-3, and mixtures thereof.

11. The composition of claim 1 further comprising a peroxisome proliferator-activated receptors (PPAR) activating fatty acid.

12. The composition according to claim 1 wherein the compound is a conjugated linoleic acid amide.

13. The composition according to claim 1 wherein the composition further comprises Vitamin A (retinol), Vitamin B2, Vitamin B3 (niacinamide), Vitamin B6, Vitamin B12, Vitamin C, Vitamin D, Vitamin E, Vitamin K, Biotin, a resorcinol or a mixture thereof.

14. The composition according to claim 1 wherein $R^1$ is hydrogen.

15. The composition according to claim 1 wherein $R^3$ is —$CH_2$—$CO_2H$.

16. The composition according to claim 1 wherein $R^1$ is hydrogen and $R^3$ is —$CH_2$—$CO_2H$.

\* \* \* \* \*